United States Patent
Daly et al.

(10) Patent No.: US 11,279,884 B2
(45) Date of Patent: *Mar. 22, 2022

(54) REVERSE FLOW REACTORS HAVING LOW MALDISTRIBUTION PARAMETER WHILE CONTAINING ASYMMETRIC FEEDS, METHODS OF USING SAME, AND PYROLYSIS PRODUCTS MADE FROM SAME

(71) Applicant: ExxonMobil Chemical Patents Inc., Baytown, TX (US)

(72) Inventors: Kevin B. Daly, Jersey City, NJ (US); Federico Barrai, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/041,012

(22) PCT Filed: Apr. 9, 2019

(86) PCT No.: PCT/US2019/026512
§ 371 (c)(1),
(2) Date: Sep. 24, 2020

(87) PCT Pub. No.: WO2019/204081
PCT Pub. Date: Oct. 24, 2019

(65) Prior Publication Data
US 2021/0139788 A1 May 13, 2021

Related U.S. Application Data

(60) Provisional application No. 62/660,310, filed on Apr. 20, 2018.

(51) Int. Cl.
*C07C 4/04* (2006.01)
*B01J 19/24* (2006.01)
(Continued)

(52) U.S. Cl.
CPC ............ *C10G 11/12* (2013.01); *B01J 19/2485* (2013.01); *C07C 4/04* (2013.01); *C10B 55/02* (2013.01);
(Continued)

(58) Field of Classification Search
None
See application file for complete search history.

(56) References Cited

U.S. PATENT DOCUMENTS 2,319,679 A    5/1943   Hasche et al.
2,678,339 A    5/1954   Harris
(Continued)

FOREIGN PATENT DOCUMENTS

GB          830574         3/1960
WO       2018/044548       3/2018

*Primary Examiner* — Philip Y Louie

(57) ABSTRACT

Reverse flow reactor (RFR) apparatuses exhibiting asymmetric feed profiles and improved flow distribution during heating mode and/or pyrolysis mode operation, and methods of using same to transform a hydrocarbon feed into a pyrolysed hydrocarbon product are disclosed. The RFR apparatus includes an RFR body with a reaction zone having at least one bed. The RFR body has a central vertical axis and is flanked by first and second void spaces. The method utilizes at least two oxygen-containing feeds, a combustion fuel feed, a purge feed, and a hydrocarbon pyrolysis feed. The RFR apparatus can cycle between an exothermic heating mode (heated to ≥700° C. while maintaining a pressure drop across the reaction zone of ≤100 kPag), a purge mode (purging oxygen using <6 bed volumes of purge gas while maintaining a pressure drop of ≤35 kPag), and an endothermic pyrolysis mode (feeding pyrolysis hydrocarbons through the reaction zone to form pyrolysis products, while maintaining a pressure drop across the reaction zone of ≤70 kPag).

16 Claims, 7 Drawing Sheets

(51) Int. Cl.
*C10G 11/12* (2006.01)
*C10B 55/02* (2006.01)
*C10G 9/26* (2006.01)

(52) U.S. Cl.
CPC ......... *B01J 2219/2419* (2013.01); *C10G 9/26* (2013.01); *C10G 2300/302* (2013.01); *C10G 2300/308* (2013.01); *C10G 2300/4006* (2013.01); *C10G 2300/4012* (2013.01); *C10G 2300/4018* (2013.01); *C10G 2400/20* (2013.01); *C10G 2400/22* (2013.01)

(56) References Cited

U.S. PATENT DOCUMENTS

| | | |
|---|---|---|
| 2,692,819 A | 10/1954 | Hasche et al. |
| 2,956,864 A | 10/1960 | Coberly |
| 2,967,205 A | 1/1961 | Coberly |
| 3,024,094 A | 3/1962 | Coberly |
| 3,093,697 A | 6/1963 | Kasbohm et al. |
| 2011/0291051 A1* | 12/2011 | Hershkowitz ............ B01J 8/048 252/373 |
| 2013/0157205 A1* | 6/2013 | Hershkowitz ......... B01F 5/0065 431/9 |
| 2014/0303416 A1* | 10/2014 | Keusenkothen ....... C10G 9/002 585/251 |
| 2021/0139789 A1* | 5/2021 | Daly ........................ B01J 6/008 |

* cited by examiner

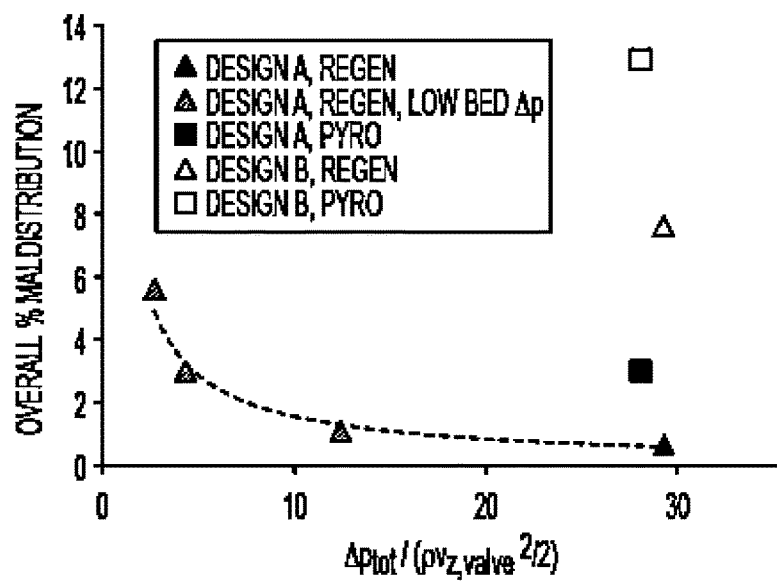
FIG. 6
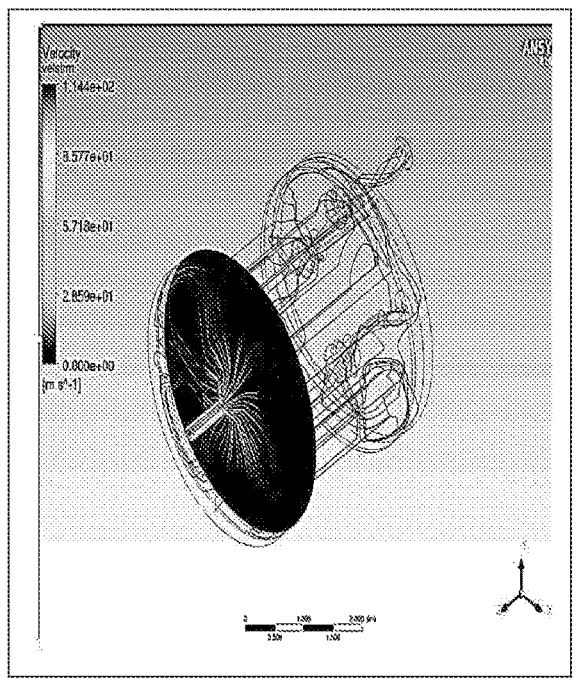 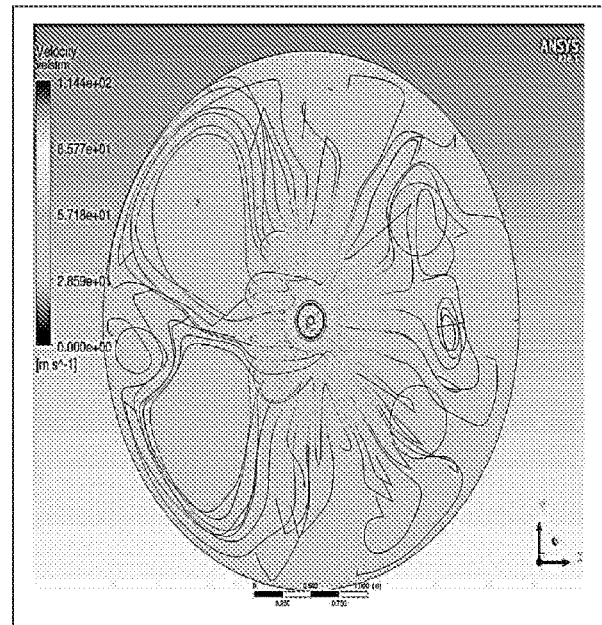
FIG. 7A  FIG. 7B

REVERSE FLOW REACTORS HAVING LOW MALDISTRIBUTION PARAMETER WHILE CONTAINING ASYMMETRIC FEEDS, METHODS OF USING SAME, AND PYROLYSIS PRODUCTS MADE FROM SAME

CROSS-REFERENCE TO RELATED APPLICATIONS

This application is a U.S. national phase application of PCT application No. PCT/US2019/026512 having a filing date of Apr. 9, 2019, which claims priority to and the benefit of U.S. provisional application Ser. No. 62/660,310 having a filing date of Apr. 20, 2018, the contents of both of which are incorporated by reference in their entirety.

FIELD

The invention relates to hydrocarbon pyrolysis, to equipment and materials useful for hydrocarbon pyrolysis, to processes for carrying out hydrocarbon pyrolysis, and to the use of hydrocarbon pyrolysis, e.g., for upgrading gaseous and liquid hydrocarbon.

BACKGROUND

This section provides background information related to the present disclosure which is not necessarily prior art.

It is conventional to produce olefinic hydrocarbon by steam cracking substantially saturated hydrocarbon in a steam cracking furnace. In a steam cracking furnace, a heating reaction and a pyrolysis reaction occur simultaneously, for example with a combustion reaction occurring on one side of partition (typically a wall or tubular) and the pyrolysis reaction on the other side. The partition between the combustion feed (e.g., reactants used during heating) and the pyrolysis feed have real physical dimensions, and the temperature is typically not equal at every location. For example, on the combustion side, temperatures may be hottest near a flame region (e.g., burner), and on the pyrolysis side temperatures can increase with heat addition until some maximum temperature is reached. However, the gases that travel through the reactor are heated and cooled by the reactions and heat transfer that takes place in the reactor.

In order to increase energy efficiency and improve the yield of light unsaturated hydrocarbon, processes have been developed which carry out hydrocarbon pyrolysis in a reverse flow reactor, ("RFR"), e.g., in a regenerative RFR. Such reactors generally include a regenerative thermal mass having at least one internal channel. The thermal mass is preheated, and then a flow of the hydrocarbon-containing feed is established through the channel. Heat is transferred from the thermal mass to the hydrocarbon feed, which increases the hydrocarbon feed's temperature and results in conversion of at least a portion of the feed by pyrolysis. The pyrolysis produces a pyrolysis product comprising molecular hydrogen, methane, acetylene, ethylene, and $C_{3+}$ hydrocarbon. The $C_{3+}$ hydrocarbon includes coke and coke precursors. Some coke remains in the passages of the thermal mass, and the remainder of the pyrolysis product is conducted away from the reactor as a pyrolysis effluent. Since the pyrolysis is endothermic, pyrolysis mode operation will eventually cool the thermal mass, e.g., to a temperature at which the pyrolysis reactions diminish or terminate. Pyrolysis conditions are restored (in other words, the reactor is regenerated for continued pyrolysis) by re-heating the thermal mass during a heating mode. The heating can be carried out, e.g., by a transfer of heat to the reactor from combustion of fuel and oxidant. During a typical heating mode, the flow of hydrocarbon-containing feed to the regenerative pyrolysis reactor is terminated. Flows of oxidant and fuel are established to the reactor, typically in an average flow direction that is substantially the reverse of the feed flow direction. Combustion of the fuel and oxidant reheats the thermal mass to a temperature sufficient for carrying out pyrolysis. The reactor can then be switched from heating mode to pyrolysis mode.

In part as a result of their utility as feeds for producing desirable products, demand for olefinic compounds ("olefin") continues to grow, particularly for light olefin such as ethylene, propylene, and butenes. Aromatic compounds, such as benzene, toluene, xylenes, naphthalene, and the like, can additionally be considered desirable product(s) from pyrolytic processes. Most commonly, olefinic compounds can be combined together to build aromatic compounds. However, this action can happen equally during cracking of a hydrocarbon feed, such as during steam cracking, with olefinic compounds perhaps being considered intermediates on the way to a product containing aromatic compounds. Along this line of logic, aromatic compounds can be considered to be intermediates on the way to coke.

Although regenerative RFRs have been used in pyrolysis reactions, the reactions are typically carried out at conditions favorable for producing alkynes such as acetylene (e.g., temperatures of greater than 1200° C. and hydrocarbon partial pressures of not greater than 7 psi). For example, the "Wulff" reactor, as described in the IHS, SRI Consulting's Process Economics Program "Acetylene" Report Number 16 (1966) and 16A (1982), and the reactors described in U.S. Pat. Nos. 2,319,679; 2,678,339; 2,692,819; 2,956,864; 2,967,205; 3,024,094; 3,093,697; and GB 830,574, are typical reverse-flow pyrolysis reactors.

There is still a need in the art, however, for improving control over the pyrolysis reaction and/or of the specific product slate made using pyrolysis. For instance, in situations where oxygen contamination is a significant issue/sensitivity, there is still a need for improved processes to purge oxygen from the pyrolysis reactor to a very low level. In another example, there is still a need for improved processes to efficiently mix reactants for more effective reactions in the pyrolysis reactor. In yet another example, there is still a need for improved processes to reduce or minimize the amount of regeneration gas needed and/or the time needed to regenerate a catalyst that may be present to facilitate the pyrolysis reaction. In still another example, there is still in a need for improved processes that allow tailoring of product slates/compositions to allow enhanced selectivity of one or more components.

SUMMARY

This section provides a general summary of the disclosure, and is not a comprehensive disclosure of its full scope or all of its features.

Certain aspects of the invention relate to methods for transforming a hydrocarbon feed (also called a "feedstream" when a flow of feed is established) into a pyrolysed product in at least one apparatus that includes at least one RFR. Such methods can include those in which the RFR apparatus can exhibit an asymmetric feed flow profile (e.g., an asymmetric flow of oxidant during heating mode) and an unfavorable (typically low) maldistribution parameter. The RFR includes at least one reaction zone, e.g., a reaction bed having the form of a tubular member, such as at least one channeled thermal mass. The channeled thermal mass has a central vertical axis and is flanked by a first void space and a second void space, which can include a support-structure void space). During one or more operating modes, the RFK may utilize various feeds, e.g., first and second feeds comprising oxidant ("first oxidant feed" and "second oxidant feed"), at least one feed comprising fuel ("fuel feed"), at least one feed comprising a purge medium ("purge feed"), and a pyrolysis feed comprising hydrocarbon. Even when feed profiles that are symmetric are introduced into an RFR apparatus, the flows still typically need to be distributed, optimally in a relatively uniform manner, for the pyrolysis reaction to be relatively homogenous within the RFR's reaction zone. This is enhanced in configurations where feeds are introduced into an RFR at locations that are asymmetric with respect to the RFR's central axis. Relative homogeneity can be expressed in relatively low maldistribution parameters, which represent ratios of pressure drop to axial kinetic energy density. The methods can include a step of operating the RFR apparatus to cycle between an exothermic heating mode, a purge mode, and an endothermic pyrolysis mode so as to attain a substantially hydrocarbon pyrolysis product. In the heating mode, the reaction zone can be heated to a temperature of at least 700° C. by reacting the combustion fuel feed with the oxygen-containing feeds while maintaining a pressure drop across the reaction zone of about 15 psig (100 kPag) or less e.g., 10 psig (70 kPag) or less. In the purge mode, oxygen can be purged from the reaction zone, advantageously using less than 6 bed volumes of purge gas from at least one of the purge feeds and under conditions sufficient to maintain a pressure drop across the reaction zone of about 5 psig (30 kPag) or less. In the pyrolysis mode, the hydrocarbons in the pyrolysis feeds can be exposed at temperature and flow conditions and for a time sufficient to pyrolyse hydrocarbon in the pyrolysis feed to form pyrolysis products, while maintaining a pressure drop across the reaction zone of 10 psig (70 kPag) or less. Optionally, in pyrolysis mode, at least one of the purge feeds can be contacted in a flow path countercurrent to the pyrolysis feeds through the reaction zone. In some cases, the heating mode can be operated under conditions such that the maldistribution parameter is at 5% or less, and such that a ratio of the pressure drop across the reaction zone to an average axial kinetic energy density of the feeds within the first and second void spaces is at least 10, e.g., between 20 and 40.

Some aspects of the invention relate to at least one apparatus that includes at least one RFR, and to operating modes and processes carried out in the RFR. The RFR comprises a reaction zone which contains at least one monolith; a first distributor having a first side adjacent to a first end of the reaction zone; a first void space adjacent to a second side of the first distributor opposite the first side; a second distributor having a first side adjacent to a second end of the reaction zone opposite the first end; a support structure disposed in a support structure volume adjacent to the second distributor opposite the first side and configured to mechanically support the monolith and the first and second distributors; and a second void space adjacent to the support structure on a side opposite the second distributor. The monolith can include at least one channel comprising a plurality of discrete passages extending axially through the monolith and having a central axis extending vertically through the monolith and contained within at least two vertical planes of symmetry. The monolith can also have a horizontal plane of symmetry perpendicular to the central axis. The RFR also includes at least (i) a first oxidant feed port for introducing a first oxidant feed into the RFR and (ii) a second oxidant feed port for introducing a second oxidant feed into the RFR. The first and second oxidant feed ports are configured to axially feed the first void space of the RFR and are arranged asymmetrically with respect to the central axis. The RFR also includes at least (i) a first pyrolysis feed port for introducing a first pyrolysis feed into the RFR and (ii) a second pyrolysis feed port for introducing a second pyrolysis feed into the RFR. The first and second pyrolysis feed ports are configured to axially introduce pyrolysis feed into the second void space of the RFR and are arranged asymmetrically with respect to the central axis. The RFR also includes at least (i) a first pyrolysis product port for removing a first portion of pyrolysis products from the RFR and (ii) a second pyrolysis product port for removing a second portion of pyrolysis products from the RFR. The first and second pyrolysis ports are each configured to axially receive a portion of the pyrolysis product from the first void space of the RFR, and are arranged asymmetrically with respect to the central axis. The RFR also includes at least (i) a first flue gas port for removing from the RFR a first portion of combustion product ("flue gas") and (ii) a second flue gas port for removing from the RFR a second portion of flue gas. The first and second flue gas ports are configured to axially receive flue gas from the second void space of the RFR, and are arranged asymmetrically with respect to the central axis. The RFR also includes a first purge port to axially feed a first purge medium into the first void space, and a second purge port to axially feed a second purge medium into the second void space. The RFR also includes at least one fuel port configured to introduce fuel into the RFR's reaction zone. In some aspects, a ratio of a volume of the first void space to a volume of the reaction zone can be 0.20 or less, a ratio of a sum of a volume of the second void space plus the support structure volume to the volume of the reaction zone can be 0.37 or less, and the RFR apparatus can be configured to operate under a pressure drop across the RFR body of up to 15.0 psig (103 kPag).

In some aspects of the invention, e.g., those relating to RFRs for hydrocarbon pyrolysis reactions, each of the two or more oxygen-containing feed ports, the two or more pyrolysis feed ports, the two or more pyrolysis product ports, the two or more flue gas ports, and the two or more purge ports can additionally or alternatively comprise a poppet valve that opens into the respective void spaces, each poppet valve exhibiting a valve head diameter A, a valve rim thickness C, a valve head clearance D, a valve shaft diameter E, and a valve inlet/outlet diameter F. In certain such aspects in which the reaction zone can have an Effective Diameter Z, at least three of the following can be satisfied: a ratio of A/Z (in m/m) ranges from 0.10 to 0.20; a ratio of C/Z (in m/m$^3$) ranges from 0.005 to 0.017; a ratio of D/Z (in m/m$^3$) ranges from 0.007 to 0.022; a ratio of E/Z (in m/m$^3$) ranges from 0.02 to 0.04; and a ratio of F/Z (in m/m$^3$) ranges from 0.075 to 0.18.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

FIGS. 4A-4B show maldistribution parameters during the pyrolysis mode in RFR designs A and B, respectively, while FIGS. 4C-4D show maldistribution parameters during the heating mode in RFR designs A and B respectively.

FIG. 6 shows a plot of flow maldistribution in different steps/modes of an ethane pyrolysis/cracking reaction versus a ratio of total pressure drop across an RFR/reaction zone to axial kinetic energy density for various RFR designs.

FIGS. 7A-7B graphically show simulated flow patterns within an RFR apparatus during the purge mode of ethane pyrolysis for RFR design A (from FIGS. 2A and 3A) in side view and perspective view, respectively, with streamlines showing stream flow entering on the left side in FIG. 7A and from behind the page in FIG. 7B.

DETAILED DESCRIPTION

Figure 1A:
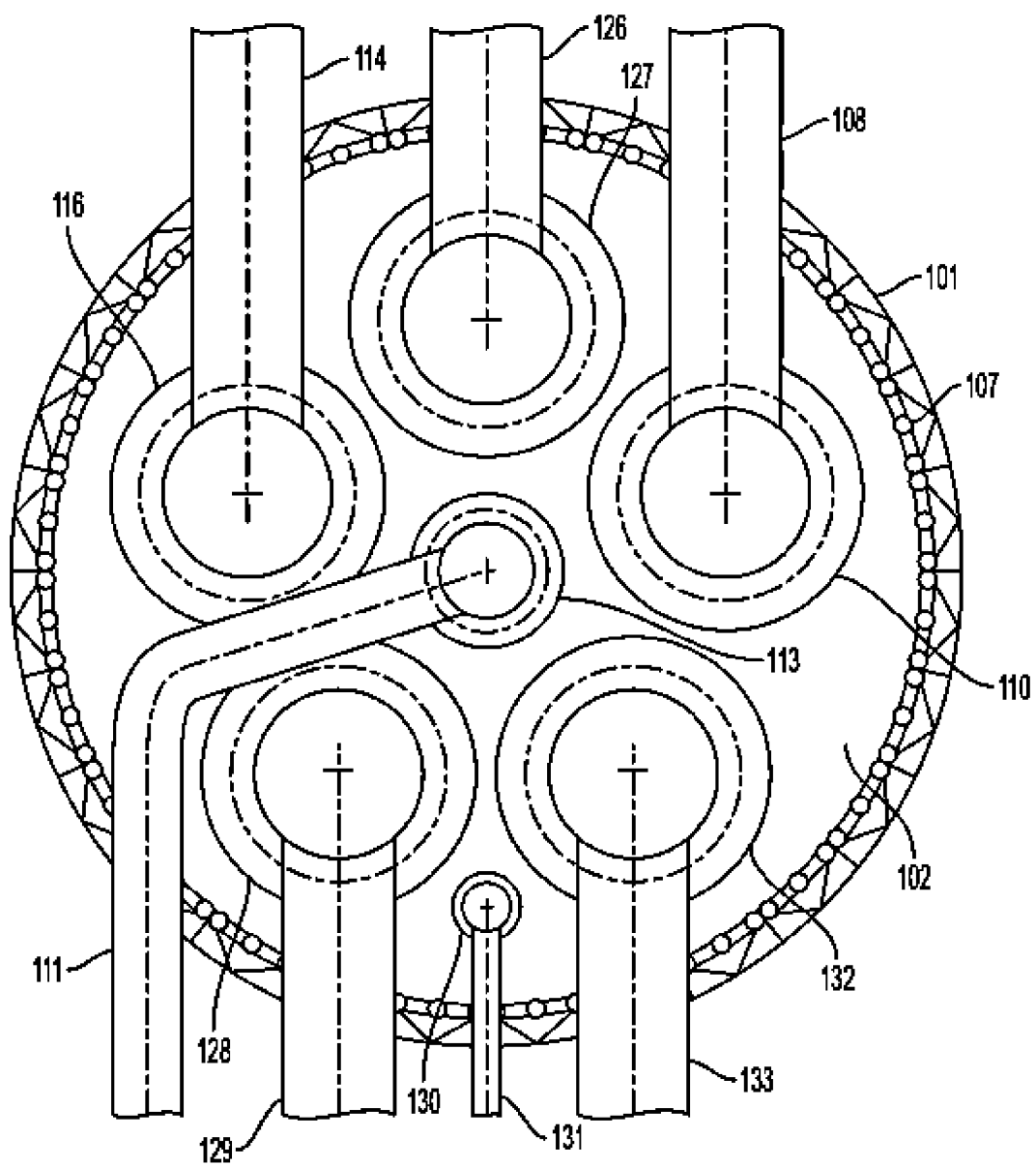
FIGS. 1A-1B are simplified end and vertical views, respectively, of a RFR having feed, product, and purge ports that are asymmetric with respect to a central vertical axis.

The invention generally relates to carrying out hydrocarbon pyrolysis in a RFR, which typically contains at least one monolith having the form of a channeled thermal mass for channeling flows of reactants and products through the RFR during its various modes of operation. Such a RFR can be employed for producing desirable products such as light olefin by operating the RFR cyclically, e.g., by carrying out in sequence (i) a step for heating mode operation to heat the thermal mass of the RFR and (ii) a step for pyrolysis mode operation that converts hydrocarbon in the pyrolysis feed to pyrolysis products. The steps may involve passing the respective streams over a solid material located in fixed orientation within the RFR (e.g., one or more thermal masses), and may utilize valves to alternate introduction of pyrolysis feed and removal of pyrolysis product (e.g., in a first average flow direction during pyrolysis mode) and the introduction fuel and oxidant and the removal of combustion products (e.g., in a second average flow direction that is substantially the reverse of the first average flow direction).

In certain aspects, the processes are carried out cyclically, e.g., by repeating a step for pyrolysis mode, a step for heating mode, a step for purge mode, and any other desired step or steps for other modes (e.g., a catalyst regeneration mode). The repeated cycles taken together can be considered as constituting a hydrocarbon processing mode. The cycle may be performed continuously, semi-continuously, or even as a batch operation. Accordingly, a cycle includes the time spent in a step for heating mode (a "heating step") plus time spent in a step for pyrolysis mode (a "pyrolysis step") plus time spent in any optional steps, e.g., a step for purge mode (a "purge step"), plus any time needed to switch between steps or for additional optional steps before the repeat of the sequence.

The RFR is heated or reheated for pyrolysis by operating the RFR in heating mode. Carrying out a heating mode imparts a profile of temperatures in the RFR, and typically in channeled thermal mass or masses within the RFR. In other words, a temperature profile is established by heating mode operating, and the temperature profile typically varies along the path by which the gases transit the RFR during heating mode. The shape of that profile depends on many factors, including if and where a heat release (combustion) reaction occurs, the initial temperature distribution, the duration of the heating step, the flow rate and inlet temperature of the gas stream, and the heat capacity and transfer properties of the gas and solid material. The region of the RFR where pyrolysis is carried out during pyrolysis mode is on-average hottest at the end of the heating mode. Pyrolysis mode operation consumes heat and changes the profile of temperatures in the RFR (particularly the temperature profile of thermal mass in the RFR). Many factors affect this temperature change, including where the heat consumption (pyrolysis) reaction occurs, the initial temperature distribution, the duration of the pyrolysis step, the flow rate and inlet temperature of the gas stream, and the heat capacity and transfer properties of the gas and solid materials in the RFR (e.g., the thermal mass). RFRs typically do not operate in the steady state during pyrolysis mode or heating mode; typically, at any given location in the RFR temperature changes as the heating and/or pyrolysis reactions progress. However, these reactors may be in a periodic steady state, meaning that the same cycling of temperatures occurs over and over as the RFR sequentially repeats the heating and pyrolysis steps, optionally with a purge step.

Certain aspects of the invention will be further defined with reference to the following definitions.

Definitions

For the purpose of this description and appended claims, the following terms are defined.

Unless specified otherwise, the term "substantially free of" with respect to a particular component means the concentration of that component in the relevant composition is no greater than 10 mol % (such as no greater than 5 mol %, no greater than 3 mol %, no greater than 1 mol %, or about 0%, within the bounds of the relevant measurement framework), based on the total quantity of the relevant composition.

The terms "periodic table", "hydrocarbon", "$C_n$" hydrocarbon, "$C_{n+}$" hydrocarbon, "$C_{n-}$" hydrocarbon, "alkane", "paraffinic hydrocarbon", "olefin", "aromatics", "aromatic hydrocarbon", "reactor", "reactor system", "regenerator", "recuperator", "regenerative bed", "monolith", "honeycomb", "conduit, "passage, "channel, "reactant", "fuel", and "oxidant", "pyrolysis", "thermal pyrolysis", "pyrolysis reactor", "pyrolysis stage", "region", "zone", "pyrolysis region", "pyrolysis zone", "regenerative reactor", "reverse flow reactor", "tubular member", "selectivity", "conversion", and "yield" have the same meaning as defined in P.C.T. Patent Application No. PCT/US2017/046937, which is incorporated by reference in its entirety.

The term RFR is used broadly, and encompasses several items that may be identified as reactors but that may be further combined to become a single entity that is also identified as a reactor. The individual and combined entities may be characterized as reactors in the sense that each concerns equipment that can be used for chemical conversion reaction.

As used herein, the "maldistribution parameter" of a step/mode/process involves an axial fluid velocity ($<Vz>$) and is defined herein as $[(<Vz^2>-<Vz>^2)^{1/2}]<Vz>*100\%$ (which is unitless). Axial fluid velocities herein represent spatial flow averages within each discrete step/mode/process. In most steps/modes/processes, the axial fluid velocity can tend to be roughly at steady state (does not tend to change significantly) throughout the step/mode/process; however, in steps/modes/processes where that is not the case, the axial fluid velocity of the relevant step/mode/process can also represent a time flow average as well as a spatial flow average.

Figure 1B:
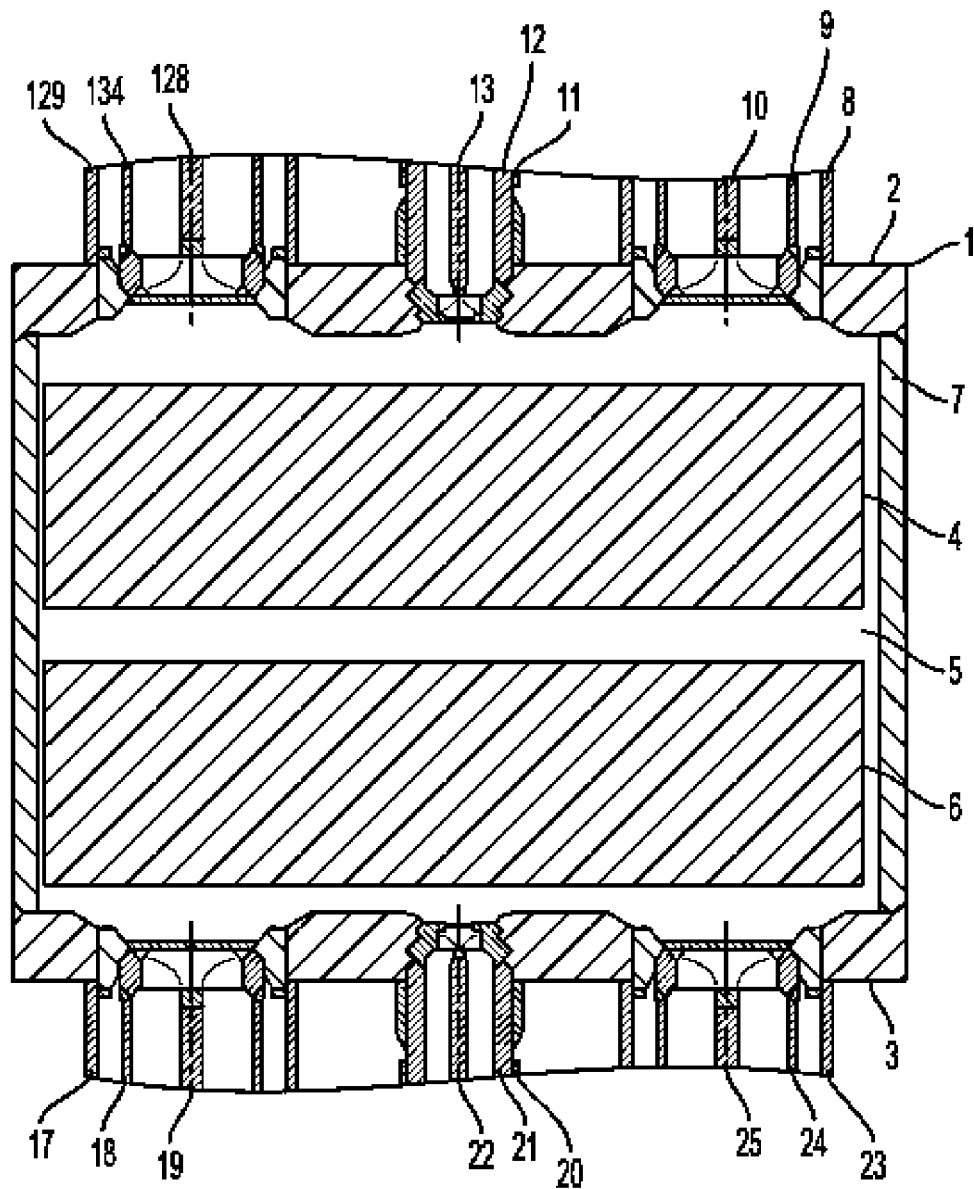

The reactors, systems of reactors, and apparatuses which include one or more reactors or systems of reactors are described herein with respect to an orientation in which the reactor's first terminal end and second terminal end represent top and bottom, such as in FIG. 1B, and such that flow thus extends in a vertical direction from top to bottom and/or from bottom to top. The reactors and/or apparatuses, as well as portions thereof, are also described herein as cylinders or prisms having a height (relative to a top-to-bottom vertical orientation) and either a circular cross-section or a regular polygonal cross-section, respectively. Regular polygons can have three or more vertices and an equal number of sides (equilateral triangle, square, regular pentagon, etc.). For odd-sided regular polygons, symmetry planes extend through the central point (representing a central axis of the prism), each vertex, and its opposite side; for even-sided polygons, symmetry planes extend through the central point (representing a central axis of the prism) and each pair of opposing vertices collinear with the central point, as well as through the central point (representing a central axis of the prism) and a center point of each pair of opposing sides, which (side) center points are also collinear with the central point (representing the central axis of the prism); for cylinders, an essentially infinite number of symmetry planes exist for each diameter of the circular cross-section of the cylinder. Therefore, with the vertical direction representing an axial direction in each case, a horizontal direction is thus orthogonal to the vertical direction and can represent either a radial direction for cylindrical apparatuses or an orthogonal direction for prism-shaped apparatuses (having regular polygonal cross-sections). The term "Effective Diameter" means (i) the diameter of cross sectional area bounded by a circular perimeter, or (ii) $2*\{SQRT [(cross sectional area)/\pi]\}$ when the cross sectional area is not bounded by a circular perimeter.

Certain RFRs for carrying out the specified pyrolysis will now be described in more detail. The invention is not limited to these RFRs, and this description is not meant to foreclose the use of other RFRs within the broader scope of the invention.

Reverse Flow Reactors

RFRs are tubular flow-through reactors having opposed terminal ends. The RFR is enclosed by a reactor body surrounding the RFRs perimeter. Each of the opposed faces of the reactor body are typically capped, e.g., with a flange, to lessen or substantially prevent leakage into and out of the RFR. The RFR includes at least one monolith, having the form of a channeled thermal mass, located in the RFR's internal volume. Besides the thermal mass, an RFR can include reactor components, such as process flow components (e.g., reactor components used to manage the flow of mixtures through the reactor) and insulation components (e.g., reactor components used to manage the heat transfer from the process flow within the reactor to the external surface of the reactor, such as insulation bricks, tiles or packing). The reactor components can be formed from different materials, such as refractory support materials.

The thermal mass comprises a tubular member having opposed first and second faces and having at least one channel, at least one of the channels having the form of a plurality of discrete passages extending axially through the member from the first face to the second face. The RFR also includes first and second void spaces. The first void space being located between the first face of the thermal mass and the first terminal end of the RFR. The second void space is located between the second face of the thermal mass and the second terminal end of the RFR. When the RFR is vertically-oriented with respect to the surface of the earth, the RFR may include at least one support structure located in the second (bottom) void space, e.g., for supporting the thermal mass. Pyrolysis reactions are carried out during pyrolysis mode in a reaction zone located within the RFR. Combustion reactions are typically carried out in during heating mode in a reaction zone located in the RFR. The location of the combustion reaction zone can be the same as the location of the pyrolysis reaction zone, but his is not required. The pyrolysis reaction zone and the combustion reaction zone can be of the same size, shape, volume, etc., but this is not required. Typically the volume of the RFR occupied by the combustion reaction zone overlaps that of the pyrolysis reaction zone. Although the pyrolysis reaction zone and combustion reaction zone each encompass at least a portion of the channeled thermal mass, it is not required that they encompass the same portion of the channeled thermal mass. The reaction zone (pyrolysis and/or combustion) can encompass an entire channeled thermal mass, or a segment thereof, which can function as a reaction bed or "bed".

The thermal mass is typically a material (e.g., a solid) that can transfer (e.g., absorb, store, and release) thermal energy over a temperature range for carrying out a reverse flow cycle, e.g., heating mode followed by pyrolysis mode. For example, the thermal mass can be a solid material that can absorb, release, and store heat to and/or from reactants and products over a temperature range in which pyrolysis can be carried out, including those that do so without any significant phase change. Examples of temperature ranges at which the thermal mass absorbs, stores, and releases thermal energy include a range of from 50° C. to 1500° C., from 100° C. to 1500° C., from 200° C. to 1500° C., from 250° C. to 1200° C., or from 300° C. to 1100° C.

The thermal mass is a channeled thermal mass having at least one channel, wherein the channel comprises at least one passages for conducting a flow of fluid. The thermal mass can comprise, e.g., refractory material, such as one or more of alumina, silica, zirconia, yttria, etc. The refractory has a mass density $\rho_s$, preferred to herein as a "solid density", and a heat capacity $C_p$ (measured at 25° C.) that is typically ≥0.05 cal./g ° C. The channeled thermal mass has an open frontal area ("OFA") for passing fluid into the channel(s), where OFA has the same meaning as in U.S. Pat. No. 5,494,881, which is incorporated by reference herein in its entirety.

When the RFK contains more than one channeled thermal mass, these can be arranged in series, one after the other from upstream to downstream. Channeled thermal masses can have the form of a sequence of segments, e.g., with or without gaps between each segment. Certain channeled thermal masses include a plurality of segments joined together, e.g., in series and/or parallel. In some aspects, the reactor can be an advanced pyrolysis reactor (APR) apparatus, such as described in U.S. Pat. No. 9,499,457, the contents of which are incorporated by reference herein. Other examples of such reactors include, but are not limited to, reverse-flow regenerative reactors as those described in U.S. Patent Application Publication No. 2007/0191664; and pyrolysis reactors as described in U.S. Pat. No. 7,491,250 and U.S. Patent Application Publication Nos. 2007/0144940 and 2008/0142409. The thermal mass elements (and regenerative beds containing them) can be in the form of a tubular member, e.g., those described in U.S. Pat. Nos. 8,754,276; 9,126,882; 9,346,728; 9,187,382; 7,943,808; 7,846,401; 7,815,873; and 9,322,549; and in U.S. Patent Application Publications Nos. 2007-0144940, 2008-300438, 2014-303339, 2014-163287, 2014-163273, 2014-0303416, 2015-166430, 2015-197696, and 2016-176781, inter alia. These references are incorporated by reference herein in their entireties.

The choice of refractory composition for a thermal mass is not critical, provided it is capable of surviving under pyrolysis mode and heating mode conditions for practical run lengths (e.g., months) without significant deterioration or decomposition. Those skilled in the art will appreciate that the compositions of the thermal mass elements should be selected from among those that substantially maintain integrity (structural and compositions) and functionality during long term exposure to pyrolysis feeds, products, and reaction conditions, e.g., temperatures≥750° C., such as ≥1200° C., or for increased operating margin≥1500° C. Conventional refractories can be used, including those comprising at least one oxide of one or more elements selected from Groups 2-14 of the Periodic Table, but the invention is not limited thereto. In particular aspects, the refractory material can include an oxide of at least one of Al, Si, Mg, Ca, Fe, Mn, Ni, Co, Cr, Ti, Hf, V, Nb, Ta, Mo, W, Sc, La, Yt, Zr, and Ce. Alternatively or in addition, the refractory material can include non-oxide ceramic. While some thermal cracking may occur upstream of the thermal mass(es) and/or the reaction zone, the reaction zone is the location or volume within the reactor where a substantial amount of the smaller molecules are produced from the initial hydrocarbons provided to the reactor.

A housing (or reactor body) encloses the interior region and the RFR. The RFR can have one or more insulation components disposed adjacent to the housing. The plurality of flow-controls may include one or more conduits, one or more apertures, and one or more valves that are configured to manage the flow of one or more streams into and out of the interior region from a location external to the interior region or housing. Process flow components can be configured and/or arranged to manage the flow of fluids through the interior region. For example, certain process flow components may include a thermal mass having a plurality of portions (e.g., a plurality of segments) with each having different flow passages and a wetted area. In some aspects, one or more mixers, distributors, or mixer-distributors can be used for mixing and/or for enhancing distribution of feed components. In other aspects, one, some, or all of the mixers, distributors, or mixer-distributors can be unnecessary and may thus be absent from the RFR. For instance, U.S. Pat. No. 9,322,549, the contents of which are incorporated by reference (except for the portions describing the value and effect of a maldistribution parameter, which may not be analogous to the maldistribution parameter disclosed herein and, if not, which portions are expressly not incorporated by reference), discloses certain benefits and detriments of mixers/flow distributors in certain RFR designs and reaction processes, particularly with respect to balancing feed distribution to the reaction zone and pressure drop therethrough. In addition, the portion of U.S. Pat. No. 7,815,873 describing mixer/flow distributors is incorporated by reference for its relevant teachings.

In certain aspects, the RFR includes a cap typically having the form of a plate-shaped member (e.g., a flange) located at the first terminal end of the RFR and sealed against the RFR housing. The cap typically includes at least one oxygen-containing feed port (e.g., two or more ports), at least one pyrolysis product port (e.g., two or more ports), at least one flue gas port (e.g., two or more ports), and at least one purge port (e.g., two or more ports). The RFR can also include a second cap having the form of a plate-shaped member (e.g., a flange) located at the second terminal end of the RFR and sealed against the RFR housing. The second cap typically includes at least one pyrolysis feed port (e.g., two or more ports), at least one flue gas port (e.g., two or more ports), and at least one purge port (e.g., two or more ports). The oxygen-containing feed port(s) can be configured to axially feed the first void space of the RFR body and can optionally but preferably be arranged asymmetrically with respect to the central axis of the reaction zone. The pyrolysis feed port(s) can be configured to axially feed the second void space of the RFR body and can optionally but preferably be arranged asymmetrically with respect to the central axis of the reaction zone. The pyrolysis product port(s) can be configured to axially receive product from the first void space of the RFR body and can optionally but preferably be arranged asymmetrically with respect to the central axis of the reaction zone. The flue gas port(s) can be configured to axially receive by-product fluids (whether gases or liquids) from the second void space of the RFR body and can optionally but preferably be arranged asymmetrically with respect to the central axis of the reaction zone. The purge port(s) can be configured to axially feed either of (or both of) the first and second void spaces of the RFR body. The combustion fuel port(s) can be configured to feed the reaction zone, optionally through a plenum and without passing through a mixer/flow distributor. In a particular aspect, the RFR can contain two oxygen-containing feed ports, two pyrolysis feed ports, three pyrolysis product ports, three flue gas ports, a combustion fuel port, and two purge gas ports, each purge gas port being configured to axially feed approximately coincident with the central axis of the reaction zone. Through some or all of these ports, valves can be utilized, e.g., to alternate introduction of a first feed mixture and/or a second feed mixture into the interior region of the reactor to contact thermal mass in the RFR.

Aspects of certain forms of RFRs will now be described with reference to FIGS. 1A and 1B. FIG. 1A is a simplified top view of an RFR having first and second oxidant ports; first, second, and third pyrolysis product ports; a purge port; and a fuel port. The flows of fluid through the ports are controlled by valves. As shown, the RFR includes reactor body 101, with refractory liner 107 positioned to protect the reactor body from contact with high-temperature materials in the reactor. Flange 102 seals the reactor body, so that fluid flow into and away from the flanged end of the RFR can be controlled by the valves. Fuel from fuel line 131 is introduced into the RFR during heating mode by opening fuel valve 130. Heating mode in these forms of FR is carried out by combusting the fuel in the RFR with oxidant introduced via first and second oxidant lines 129 and 133 and first and second oxidant valves 128 and 132. Combustion effluent is conducted away from an opposed end of the RFR (not shown in FIG. 1A). Pyrolysis mode is carried out in the heated RFR to produce pyrolysis products. Form a pyrolysis feed. Pyrolysis products produced during pyrolysis mode are removed from the RFR via first, second, and third pyrolysis product valves 110, 127, and 116, and the pyrolysis products are conducted away via lines 108, 126, and 114. Pyrolysis feed is introduced into the RFR during pyrolysis mode via the opposed end of the RFR (not shown in FIG. 1A). A purge fluid (e.g., steam) is introduced into the RFR via purge line 111 and purge valve 113 during a purge mode, which can follow the heating mode and/or the pyrolysis mode. Purged material is removed from the RFR via the opposed end of the RFR (not shown in FIG. 1A). A purge mode can be carried out following pyrolysis mode and/or following combustion mode. During a purge mode following a combustion mode, for example, oxygen can be purged from the reaction zone by flowing through the reaction zone a volume of purge gas that is some a factor ("$F_P$") times the bed volume (at reaction temperature and pressure), e.g., through the thermal mass when the thermal mass corresponds to the reaction zone. $F_P$ is typically in the range of from 0.5 to 20, e.g., from 1 to 10, or from 3 to 9.

FIG. 1B is a simplified cross sectional view of an RFR having a similar configuration to that of FIG. 1A. The RFR of FIG. 1B includes a tubular reactor body 1 terminated at its ends in first and second flanges 2 and 3. First 4 and second 6 thermal masses, each configured as a tubular member (for simplicity, the passages are not shown), are positioned in the RFR. The reactor body is protected from the sides of the thermal masses by refractory lines 7. The inner surface of flange 2 is separated from the outer surface of first thermal mass 4 by a spacing called a "headspace". The outer surface of second thermal mass 6 is separated from the inner surface of second flange 3 by a spacing called an "outage". The opposed inner faces of thermal masses 4 and 6 are separated by a mixing/distribution zone 5, where at least a portion of the fuel and the oxidant combine and combust during heating mode. During heating mode, fuel is introduced into the RFR through flange 2 (fuel line and valve not shown in FIG. 1B) for combustion with oxidant. A first portion of the oxidant is introduced into the RFR via a first oxidant line 129, with the flow of this portion being controlled by first oxidant valve 128 opening and closing against valve seat 134. A second portion of the oxidant is introduced into the RFR through first flange 2 via a second oxidant line and second oxidant valve (not shown in FIG. 1B). Combustion products are conducted through flange 3 via combustion product line 23, the flow being controlled by combustion product valve 25 operating against valve seat 24. A purge medium, e.g., steam, molecular nitrogen, inert gas, etc., can be introduced into the RFR via purge line 11, with the flow of purge medium into the RFR being controlled by purge valve 12 opening and closing against valve seat 12. When a purge mode is carried out during and/or after a heating mode, purge material can be removed from the RFR, e.g., via line 23 by opening or maintaining an opening between valve 25 and valve seat 24.

During pyrolysis mode, a pyrolysis feed is introduced into the heated RFR through second flange 3 via pyrolysis feed line 17. The average flow direction of fluid through the RFR during pyrolysis mode is substantially the reverse of that during heating mode. In other words, an "upstream" component of the RFR during heating becomes a "downstream" component during pyrolysis mode, and vice versa. As in heating mode, the fluid flows during pyrolysis mode are controlled using valves. The flow of pyrolysis feed is controlled by opening and closing pyrolysis feed valve 19 against valve seat 18. The pyrolysis feed is heated in the internal passages of the upstream section of second thermal mass 6. Pyrolysis conditions are typically achieved in the downstream section of thermal mass 6 and in mixing distribution zone 5. Heat is transferred form the pyrolysis products in the internal channels of first thermal mass 4, and the cooled pyrolysis product is conducted away from the RFR via first pyrolysis product line 8. The flow of pyrolysis products away from the RFR via line 8 is controlled by first pyrolysis product valve 10 opening and closing against valve seat 9. The second and third pyrolysis product lines (and associated valves and valve seats) are not shown in FIG. 1B. A second purge medium, e.g., steam, molecular nitrogen, inert gas, etc., can be introduced into the RFR via second purge line 20, with the flow of purge medium into the RFR being controlled by second purge valve 22 opening and closing against valve seat 21. When a purge mode is carried out during and/or after a pyrolysis mode, purge material can be removed from the RFR, e.g., via line 8 by opening or maintaining an opening between valve 10 and valve seat 9.

In these aspects, the locations of the functional zones in the RFR are not at fixed positions. During heating mode, the reaction zone (combustion region in this case) is mainly in mixing/distributing zone 5. During pyrolysis mode, the reaction zone (the pyrolysis region in this case) is mainly in passages within the downstream section of second thermal mass 6 and in mixing/distribution zone 5. Further, during pyrolysis mode, (i) the upstream section of second thermal mass 6 is a preheating zone for heating the pyrolysis feed to a temperature sufficient for pyrolysis to occur, and (ii) most if not all of first thermal mass 4 is a cooling zone, for transferring heat away from the pyrolysis products. During heating mode, (i) most if not all of first thermal mass 4 functions as a preheating zone for heating at least the oxidant needed for combustion, and (ii) most if not all of second thermal mass 6 is a cooling zone for transferring heat away from the combustion products. In other words, cooler thermal mass zones can absorb heat from the pyrolysis product mixture during a first time interval for pyrolysis mode, sufficient to (i) cool or quench the product mixture from pyrolysis of hydrocarbon in the pyrolysis feed stream and (ii) impart heat to oxidant (and optionally fuel) streams during heating mode, when the flow is reversed during a second time interval (reverse-flow). Translation, widening, and narrowing of the RFR's zones can occur as the various modes progress.

In many RFRs, gaseous feed enters from an end of the reactor and should be distributed as evenly as possible across an array of substantially one-dimensional plug-flow (monolith) passages in the channeled thermal masses, in order to increase/maximize yields and/or reactor safety. In many forms of RFR, fluid (e.g., steam) can enter the reactor through a relatively small number of ports (e.g., only 2 poppet valves), in some cases oriented asymmetrically relative to a central axis or a center of mass of the reactor/ reaction zone, in order to decrease/minimize reactor and piping layout costs (see, for example, FIGS. 1A-1B). The use of poppet valves as feed and/or product ports in RFRs is conventional—see, e.g., U.S. Patent Application Publication No. 2011/0291051, which is incorporated by reference herein. In order to target the combustible fuel stream delivery, unlike most of the other feed and product streams/ports, the combustible fuel can be provided to the RFR body (thermal mass(es) within the reaction zone) e.g., through the use of a plenum or even direct injection into the combustion zone.

Hence, it can be particularly desirable for the reactor volume between the ports (valves) and the opposed face of the channeled thermal mass to be precisely designed or managed to dramatically distribute or homogenize feed flow before it contacts the monolithic thermal mass. In some RFR processes, such as light hydrocarbon cracking, one key constraint on reactor design can be to reduce/minimize the total volume between the ports (valves) and the monolith to be small enough to enable rapid switching between process steps, thus increasing/maximizing reactor process efficiency. For instance, following the combustion reaction in the heating step of light ($C_{4-}$) hydrocarbon cracking, a rapid purge of the reaction zone (e.g., with steam) can be beneficial before starting the pyrolysis step. Excessive void volume above and below the monolith might otherwise increase the amount of purge gas and/or the time needed to execute an appropriately complete purge step.

Because ports are typically present on both terminal ends of a RFR, there are typically void volumes at both top and bottom of a vertically oriented RFR reaction zone for distribution and/or redistribution of feed flow. However, because the bottom of a vertically oriented RFR reaction zone can typically have mechanical structure (such as support beams) to support the weight of the components within the reactor, the bottom void space typically contains a support structure volume (which houses the mechanical support structure) and a bottom void volume (the "outage" as previously defined). For instance, the mechanical support structure can be disposed in the support structure volume between the second void space (outage) and the second mixer/distributor and can be configured to mechanically support the monolithic reaction zone (as well as the first and second mixer/distributors, if either are present). In comparison, the top void space typically contains no support structure volume (nor significant mechanical support structure) and thus typically contains only a top void volume (the "headspace" as defined above). See FIGS. 1A-1B and 2A-2B. In various aspects, the volumes of the headspace and outage, as well as ratios containing them, can be varied to tailor flow equalization/distribution through the RFR, for instance to increase/maximize the efficiency of one or more of the process steps, whether in absolute terms or relative to one or more other process steps.

For example, in some aspects, a ratio of a volume of the first void space (top end; headspace) to a volume of the reaction zone can be 0.10 or less, e.g., 0.090 or less, 0.080 or less, 0.075 or less, 0.070 or less, 0.065 or less, 0.060 or less, 0.055 or less, 0.050 or less, 0.045 or less, 0.040 or less, 0.035 or less, 0.030 or less, 0.025 or less, or 0.020 or less; optionally, the ratio of the volume of the first void space (top end; headspace) to the volume of the reaction zone can additionally be at least 0.008, at least 0.010, at least 0.012, at least 0.016, at least 0.020, at least 0.025, at least 0.030, at least 0.035, at least 0.040, at least 0.045, at least 0.050, at least 0.055, or at least 0.060. In particular aspects, the ratio of the volume of the first void space (top end; headspace) to the volume of the reaction zone can be from 0.025 to 0.10, from 0.020 to 0.070, from 0.012 to 0.035, or from 0.016 to 0.060.

Additionally or alternatively, in some aspects, a ratio of a sum of a volume of the second void space (bottom end; outage plus the support structure volume) to the volume of the reaction zone can be 0.20 or less, 0.19 or less, 0.18 or less, 0.17 or less, 0.16 or less, 0.15 or less, 0.14 or less, 0.13 or less, 0.12 or less, 0.11 or less, 0.10 or less, 0.090 or less, 0.080 or less, 0.070 or less, 0.060 or less, 0.050 or less, or 0.040 or less; optionally, the ratio of the sum of a volume of the second void space (bottom end; outage) plus the support structure volume to the volume of the reaction zone can be at least 0.020, at least 0.025, at least 0.030, at least 0.035, at least 0.040, at least 0.050, at least 0.060, at least 0.070, at least 0.080, at least 0.090, at least 0.10, at least 0.11, at least 0.12, or at least 0.13. In particular aspects, the ratio of the sum of a volume of the second void space (bottom end; outage) plus the support structure volume to the volume of the reaction zone can be from 0.040 to 0.13, from 0.080 to 0.16, from 0.030 to 0.10, or from 0.025 to 0.15.

Additionally or alternatively in some aspects, the volume encapsulating the support structure can be accompanied by substantially no additional second void space (bottom end; outage), leaving only the support structure volume at the bottom end. In such aspects, a ratio of the support structure volume to the volume of the reaction zone can be 0.13 or less, 0.12 or less, 0.11 or less, 0.10 or less, 0.090 or less, 0.080 or less, 0.070 or less, 0.065 or less, 0.060 or less, 0.055 or less, 0.050 or less, 0.045 or less, 0.040 or less, 0.035 or less, or 0.030 or less; optionally, the ratio of the support structure volume to the volume of the reaction zone can be at least 0.015, at least 0.020, at least 0.025, at least 0.030, at least 0.040, at least 0.050, at least 0.060, at least 0.070, at least 0.080, or at least 0.090. In particular aspects, the ratio of the support structure volume to the volume of the reaction zone can be from 0.030 to 0.090, from 0.015 to 0.080, or from 0.025 to 0.11.

Figure 2A:
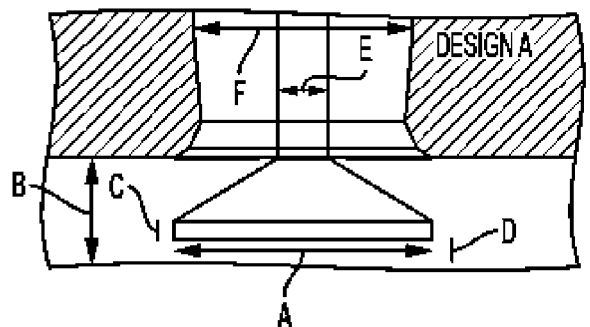
FIGS. 2A-2B show a vertical cross-sectional view of a port poppet valve structure for a moderate void-volume RFR design (design A) and a low void-volume RFR design (design B), respectively, showing various lettered aspects of the valve structure.
Figure 2B:
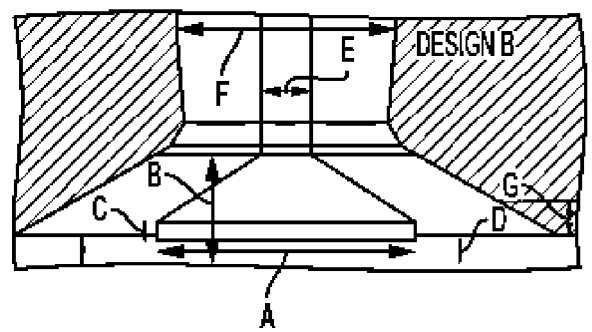
Figure 3A:
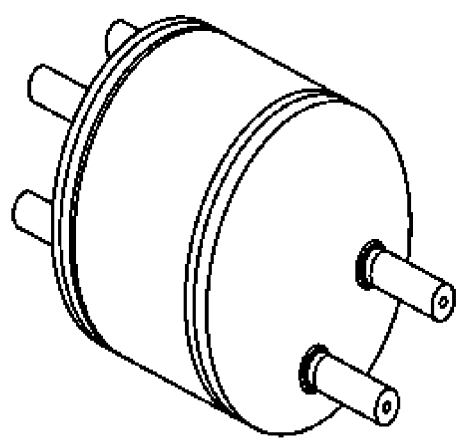
FIGS. 3A-3B show solid perspective views (bottom/outage side forward, showing two oxygen-containing feed ports asymmetrically disposed thereon, and three corresponding flue gas ports asymmetrically disposed on the far/headspace side) of a moderate void volume RFR design (design A) and a low void volume RFR design (design B), respectively.
Figure 3B:
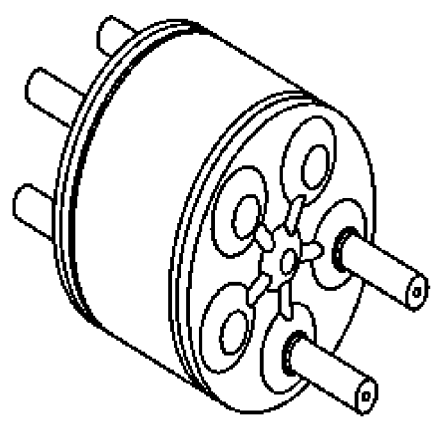

In other aspects (not shown), an alternative (and somewhat simplified) RFR is used. The alternative RFR can comprise a reactor body having an interior volume bounded by opposed first and second terminal ends. The interior volume includes one monolithic channeled thermal mass in substitution for the first thermal mass, second thermal mass, and mixing/distribution zone of the RFR illustrated in FIG. 1B. The channeled thermal mass includes a plurality of discrete channels extending axially through the thermal mass from a first outer face to a second outer face. The channeled thermal mass also has a central axis extending vertically therethrough and contained within at least two vertical planes of symmetry, and a horizontal plane of symmetry perpendicular to the central axis. The RFR has a first void volume located between the first terminal end of the RFR and the outer face of the channeled thermal mass. The RFR also has a second void volume located between the second terminal end of the RFR and the outer face of the channeled thermal mass. The first and second void volumes and the open volume located between the opposed faces of the channeled thermal mass define a reactor volume (total internal volume). The reaction zone (combustion during heating mode and pyrolysis during pyrolysis mode, as the case may be) is located in the reactor volume. The reaction zone has an Effective Diameter Z. The reaction zone is the region within the reactor's internal volume where a reaction is carried out, e.g., combustion and/or pyrolysis as the case may be. Depending on the reaction type, reaction conditions, and the configuration of the RFR's internal volume, the reaction zone can include one or more of the following RFR components and regions: (i) at least a portion of the monolith; (ii) a first distributor (or mixer or mixer-distributor) located in the first void volume and having an outer face adjacent to the first terminal end (e.g., inner surface of a top flange) of the RFR; (iii) a first void space (a headspace) located between the inner face of the first distributor and the first outer face of the channeled thermal mass; (iv) a second distributor (or mixer or mixer-distributor) located in the second void volume and having an outer face adjacent to the second terminal end (e.g., inner face or a bottom flange) of the RFR; and (v) a second void space (outage) located between the inner face of the second distributor and the second outer face of the channeled thermal mass. In various lettered aspects, one, some, or all of the feed and/or product ports of the alternative RFR can comprise a poppet valve opening toward the reaction zone. The poppet valve opens into the first or second void space (as the case may be) and can exhibit a valve head diameter A, a valve rim thickness C, a valve head clearance D, a valve shaft diameter E, a valve inlet/outlet diameter F; and optionally a passage, such as substantially semi-circular passage having a height G, in fluidic communication with at least a second valve, as illustrated in FIGS. 2A-2B. For clarity, it should be understood that the valve head clearance D represents the orthogonal distance from the end of the valve head to a border of the respective void space nearest the reaction zone. In addition, the first void space can have an axial height B1, the second void space can have an axial height B2, and the support structure volume can have an axial height BS. Lines connected to these valves, e.g., for conveying oxidant to the alternative RFR (two lines) and for conveying combustion product away from the RFR (three lines) are illustrated in FIGS. 3A and 3B. For simplicity of illustration, the pyrolysis feed line(s), pyrolysis product line(s), purge line(s), and their associated valves and valve seats are not shown in FIGS. 3A and 3B.

A wide range of reactor and component sizes, e.g., valve dimensions, etc., can be used. For example, reactor volume (internal volume) can be, e.g., $\geq 0.1$ m$^3$, or $\geq 1$ m$^3$, or $\geq 10$ m$^3$, or $\leq 100$ m$^3$, or $\leq 10$ m$^3$, or $\leq 1$ m$^3$. In certain aspects, the reactor volume is in the range of from 1 m$^3$ to 50 m$^3$, although larger or smaller reactor volumes can be used. Head space volume (and to a lesser extent, outage volume) is determined largely by the valve size, the position of the inner face of the flange with respect to the reaction zone, and the distance between the inner face of the flange and the valve face. A wide range of volumes can be used, depending on the reactor configuration, e.g., a headspace (or outage) volume$\leq 50$ m$^3$, or $\leq 10$ m$^3$, or $\leq 5$ m$^3$, or $\geq 0.1$ m$^3$, or $\geq 1$ m$^3$, or $\geq 10$ m$^3$, such as in the range of from 1 m$^3$ to 10 m$^3$.

In certain aspects, the reaction zone's Effective Diameter Z has substantially the same value in combustion mode as in pyrolysis mode, e.g., Z$\geq 1$ cm, or $\geq 10$ cm, or $\geq 100$ cm, or more; or $\leq 500$ cm, or $\leq 50$ cm, or $\leq 5$ cm, or $\leq 0.5$ cm, such as in the range of from 50 cm to 500 cm. In these or other aspects, (i) A is typically $\geq 0.25$ cm, or $\geq 2.5$ cm, or $\geq 25$ cm, or $\leq 75$ cm, or $\leq 7.5$ cm, or $\leq 0.75$ cm, e.g., in the range of from 10 cm to 90 cm; (ii) B is typically $\geq 0.1$ cm, or $\geq 1.0$ cm, or $\geq 10$ cm, or $\geq 50$ cm, or $\leq 5$ cm, or $\leq 0.5$ cm, e.g., in the range of from 1 cm to 50 cm; (iii) C is typically $\geq 0.1$ cm, or $\geq 1$ cm, or $\geq 10$ cm, or $\leq 100$ cm, or $\leq 10$ cm, or $\leq 1$ cm, e.g., in the range of from 1 cm to 10 cm; D is typically $\geq 0.1$ cm, or $\geq 1$ cm, or $\geq 10$ cm, or $\leq 100$ cm, or $\leq 10$ cm, or $\leq 1$ cm, e.g., in the range of from 1 cm to 10 cm; E is typically $\geq 1$ cm, or $\geq 10$ cm, or $\geq 100$ cm, or $\leq 1000$ cm, or $\leq 100$ cm, or $\leq 10$ cm, e.g., in the range of from 1 cm to 20 cm; F is typically $\geq 1$ cm, or $\geq 10$ cm, or $\geq 100$ cm, or $\leq 100$ cm, or $\leq 10$ cm, or $\leq 1$ cm, e.g., in the range of from 10 cm to 100 cm. In aspects where the valve recesses are connected by passages of height G (e.g., design B), G is typically $\geq 0.1$ cm, or $\geq 1$ cm, or $\geq 10$ cm, or $\leq 100$ cm, or $\leq 10$ cm, or $\leq 1$ cm, e.g., in the range of from 1 cm to 10 cm.

In certain aspects, at least one of the reactor's valves satisfies one or more of the following relationships: A/Z$\leq 0.19$, or $\leq 0.17$, or $\leq 0.15$, or $\leq 0.13$, or $\geq 0.12$, or $\geq 0.14$, or $\geq 0.16$, or $\geq 0.18$, e.g., in the range of from 0.1 to 0.2; (ii) C/Z$\leq 0.016$, or $\leq 0.014$, or $\leq 0.012$, or $\leq 0.010$, $\leq 0.008$ or $\geq 0.006$, or $\geq 0.008$, or $\geq 0.010$, or $\geq 0.012$, or $\geq 0.014$, e.g., in the range of from 0.005 to 0.017; (iii) D/Z$\leq 0.020$, or $\leq 0.016$, or $\leq 0.012$, or $\leq 0.008$ or $\geq 0.010$, or $\geq 0.14$, or $\geq 0.018$, e.g., in the range of from 0.007 to 0.022; (iv) E/Z$\leq 0.035$, or $\leq 0.030$, or $\leq 0.025$, or $\geq 0.025$, or $\geq 0.030$, or $\geq 0.025$, e.g., in the range of from 0.02 to 0.04; (iv) F/Z$\leq 0.16$, or $\leq 0.14$, or $\leq 0.12$, or $\leq 0.10$, $\leq 0.09$ or $\geq 0.09$, or $\geq 0.10$, or $\geq 0.11$, or $\geq 0.12$, or $\geq 0.14$, e.g., in the range of from 0.005 to 0.018; and. G/Z can be $\leq 0.025$, $\leq 0.020$, or $\leq 0.015$, or $\leq 0.010$, or $\geq 0.010$, or $\geq 0.015$, or $\geq 0.20$, or $\geq 0.25$, e.g., in the range of from 0.009 to 0.033.

The dimensions of valve components can also be expressed in terms of distance ratios, e.g., as one or more of (i) B1/Z can be $\geq 0.02$, or $\geq 0.05$, or $\geq 0.08$, or $\leq 0.08$, or $\leq 0.06$, or $\leq 0.04$, e.g., in the range of from 0.01 to 0.1; (ii) B2/Z can be $\geq 0.02$, or $\geq 0.05$, or $\geq 0.08$, or 0.08, or $\leq 0.06$, or $\leq 0.04$, e.g., in the range of from 0.01 to 0.1; and (iii) BS/Z$\geq 0.02$, or $\geq 0.05$, or $\geq 0.08$, or $\leq 0.08$, or $\leq 0.06$, or $\leq 0.04$, e.g., in the range of from 0.01 to 0.1.

The specified RFR can be operated in various modes, e.g., heating mode, pyrolysis mode, purge mode, catalyst regeneration mode, etc., in order to produce the desired products, e.g., light olefin. Heating mode is typically carried out for a time duration $t_H$ to achieve a desired temperature profile in the internal volume of the RFR for the start of pyrolysis mode, primarily by fuel-oxidant combustion in the combustion zone, coke-oxidant combustion in passages of channeled thermal masses in the RFR, and optionally additional fuel-oxidant combustion outside of the combustion zone, e.g., within internal passages of one or more thermal masses in the RFR. Pyrolysis mode is typically carried out for a time interval $t_P$. Pyrolysis is endothermic, and, consequently, the bulk gas temperature profile of the RFR is transformed over the course $t_P$ to one that is not appropriate for efficient pyrolysis. Additional modes, e.g., heating mode, purge mode, catalyst regeneration mode etc., can then be carried out to prepare the RFR for further pyrolysis mode operation, e.g., by carrying out a heating mode to establish in the RFR a desired bulk gas temperature profile for pyrolysis mode. Valves associated with the specified RFR, e.g., those of FIGS. 1A and 1B, can be used to (i) establish forward flows of the pyrolysis feed and the pyrolysis product during pyrolysis mode for a time duration $t_P$, (ii) establish reverse flows of the fuel, the oxidant, and the combustion product during heating mode for a time duration $t_H$, and (iii) establish other flows for other modes, e.g., purge gas flow for purge mode. The valve means can be operated by one or more flow controllers.

Pyrolysis mode and heating mode are typically repeated in sequence, for semi-continuous or continuous operation. Intervening steps between successive pyrolysis and heating modes, e.g., one or more steps for admitting a forward or reverse flow of sweep gas to the reverse-flow reactor, can be carried out between pyrolysis mode and heating mode operation, and vice versa. Continuous or semi-continuous operation can be characterized by a "cycle time", which constitutes the time duration from the start of a pyrolysis mode to the start of the next pyrolysis mode in the sequence, and includes the time duration of heating mode(s) and any intervening steps (when used). Cycle time can be substantially constant over a plurality of repeated cycles, but this is not required. The specified RFR is compatible with relatively short cycle times compared to that of conventional processes for pyrolysing similar feed hydrocarbon at a peak pyrolysis temperature$\leq 1200°$ C. For example, cycle can be ≤60 seconds, e.g., ≤30 seconds, such as ≤15 seconds, or ≤5 seconds, or ≤1 second, or ≤0.1 second. Typically, cycle time is in the range of from 0.1 second to 60 seconds, e.g., 0.1 second to 15 seconds, such as 0.1 second to 10 seconds, or 0.1 second to 5 seconds, or 0.1 second to 1 second.

Certain aspects of heating mode operation will now be described in more detail. The invention is not limited to these aspects, and this description is not meant to foreclose other ways to operate a heating mode within the broader scope of the invention.

RFR Heating Mode

In certain aspects, heating mode includes combusting fuel and oxidant in a combustion zone of the RFR. Particularly when the pyrolysis reaction is operated under high-severity conditions and/or for a prolonged residence time or cycle time, the pyrolysis can produce undesirable or less desirable products such as coke. When that happens, coke formed can be catalytic itself, transforming a desirable product into more coke. In aspects where coke accumulation is detrimental, heating mode operation can also remove such undesirable products as coke, e.g., by combustion of the coke such as via oxidation with an oxygen-containing stream. In non-catalytic systems, or in systems where coke accumulation is minimal or nonexistent, the heating mode can simply involve the "regeneration" (namely the reheating) of the heat source in the RFR for the endothermic pyrolysis reaction. Although the prior art sometimes refers to heating mode as "regeneration mode", it is considered beneficial in this description to make a distinction between a step for RFR regeneration (called "heating mode" or "heating step" in this description) and a step for RFR catalyst regeneration (called a "catalyst regeneration step" or "catalyst regeneration mode" in this description). In certain aspects, e.g., when a catalyst associated with the RFR (e.g., a catalyst in or on a thermal mass of the RFR) can be regenerated by contact with oxidant, the heating step can also serve as a catalyst regeneration step. Thus, in various aspects, one or both regenerative goals (RFR reheating and catalyst regeneration) can be achieved by addition of an oxygen-containing stream (through one or more oxygen-containing feed ports) and a (hydrocarbon) fuel stream (through one or more combustion fuel feed ports) to a reaction zone that has attained a certain level of undesirable or less desirable products such as coke.

The combustion fuel feed and the oxygen-containing feed can be mixed at or prior to entering the reaction zone, e.g., by initially flowing at least the oxidant and typically also the fuel to the reaction zone through a combustion-gas preheating zone in separate channels of a thermal mass. For instance, fuel and oxidant can be separately introduced into the reactor and separately flowed through separate channels of a honeycomb channel arrangement in portions of the thermal mass located upstream of the reaction zone, e.g., through separate channels of first thermal mass 4 of FIG. 1 B. The combustion fuel feed and the oxygen-containing feed can typically be heated as they flow through the channels, e.g., by heat transferred to these portions during quenching of pyrolysis products during a preceding pyrolysis step. Following heating, the combustion fuel feed and the oxygen-containing feed can then be mixed in situ, so that combustion can take place, e.g., in mixing/distributing zone 5 the aspect illustrated in FIG. 1 B.

Typically, the combustion zone (e.g., mixer/distributor zone 5 in FIG. 1B) is heated to a temperatures of at least 700° C. (e.g., at least 750° C., at least 800° C., at least 850° C., at least 900° C., at least 950° C., at least 1000° C., at least 1050° C., at least 1100° C., at least 1150° C., or at least 1200° C.; optionally up to 1600° C., up to 1500° C., up to 1400° C., up to 1350° C., up to 1300° C., up to 1250° C., or up to 1200° C.) by reacting the combustion fuel feed with the oxygen-containing feeds. If a catalyst is utilized in the pyrolysis process, then the heating mode can advantageously be effective to at least partially (in some aspects, substantially) regenerate the catalyst.

In some aspects, the reaction zone can be regenerated at a pressure comparable to that used during operation of the pyrolysis mode. In some aspects, the reaction zone can be regenerated using a total pressure of ≥5 psig (30 kPag), ≥15 psig (100 kPag), ≥40 psig (280 kPag), ≥80 psig (550 kPag), or ≥120 psig (830 kPag). For practical considerations on total pressure, the heating mode can be carried out at a total pressure of ≤500 psig (3.5 MPag), ≤300 psig (2.1 MPag), or ≤150 psig (1.0 MPag).

Any convenient fuel and oxidant reactants can be used for the specified combustion reaction during heating mode, including those disclosed in U.S. Pat. No. 9,499,457 and in P.C.T. Patent Application No. PCT/US2017/046937, but the invention is not limited thereto. Heating mode conditions can be, e.g., the same as those disclosed in U.S. Pat. No. 9,499,457 and in P.C.T. Patent Application No. PCT/US2017/046937, particularly when the desired pyrolysis products comprise $C_{4-}$ olefin.

In various aspects, in order to achieve relatively stable component flow patterns/distributions (optimally unchanging during any given mode), it can be desirable to achieve at least a threshold ratio of a pressure drop across the reaction zone (including a distributor, if present, as well as any reactor internals, if present) to an axial kinetic energy density at the inlet(s) (e.g., poppet valves) to the RFR body (at the entrance to the first and/or second void spaces; for instance, at the valve curtain) during most reaction steps/modes, but particularly during the heating mode. The threshold ratio of pressure drop across the reaction zone to axial kinetic energy density can be at least 5, e.g., at least 10, at least 15, at least 20, at least 25, at least 30, at least 35, or at least 40. Without being bound by theory, it is believed that, above a certain threshold ratio, component flow patterns can stabilize, such that distribution (perhaps expressed via maldistribution parameter) can be relatively constant or repeatable. As such, there need not be a maximum imposed on threshold ratio of pressure drop across the reaction zone to axial kinetic energy density; nevertheless, optionally the threshold ratio of a pressure drop across the reaction zone to an axial kinetic energy density can additionally be 1000 or less, e.g., 500 or less, 100 or less, 80 or less, 70 or less, 60 or less, 50 or less, 40 or less, 35 or less, or 30 or less. Thus, it can be desirable to achieve a relatively low maldistribution parameter (ratio of pressure drop to axial kinetic energy density) during most reaction steps/modes, but particularly during the heating mode. A relatively low maldistribution parameter can be 15% or less, e.g., 14% or less, 13% or less, 12% or less, 11% or less, 10% or less, 9% or less, 8% or less, 7% or less, 6% or less, 5% or less, 4% or less, or 3% or less.

After heating mode has been completed and any optional modes (e.g., purge modes and/or catalyst regeneration modes) have been carried out, the RFR is in condition for pyrolysis mode operation. Certain aspects of pyrolysis mode operation will now be described in more detail. The invention is not limited to these aspects, and this description is not meant to foreclose other ways to operate a pyrolysis mode within the broader scope of the invention.

RFR Pyrolysis Mode

During pyrolysis mode, pyrolysis feed comprised of hydrocarbons, and optionally diluent, can be supplied to or injected into an end of the reactor via pyrolysis injection components. The pyrolysis feed may be supplied to or injected into the pyrolysis reactor following the removal of the combustion products from the heating step, which may be supplemented by a purge mode for sweeping and/or purging from the RFR undesirable products of a heating step from the internal regions of the entire reactor. That is, the pyrolysis stream can be configured to flow through the first and/or second end of the thermal mass of a RFR. The pyrolysis feed used during pyrolysis mode is typically provided at a different end (typically an opposed end) of the RFR from the end supplying the combustion feeds (typically oxidant and fuel) during heating mode. In other words, direction of flow of the pyrolysis feed may be counter to (e.g., reverse of) the direction of flow of at least the oxidant portion of the combustion feed (and typically also the reverse of the fuel flow, which can be parallel to oxidant flow), or in certain aspects may be in the same direction, which may also involve some alternating patterns of flow.

In certain aspects, the pyrolysis feed flows through a pyrolysis preheat zone, e.g., within upstream segments of passages of channeled thermal mass 6 of FIG. 1 B, to increase the temperature of the pyrolysis. As the temperature increases to the appropriate level, pyrolysis of the hydrocarbon in the pyrolysis feed takes place, e.g., in downstream segments of channeled thermal mass 6 and in mixing/distribution zone 5. Those skilled in the art will appreciate that although region 5 of FIG. 1B is referred to as a "mixing/distribution zone", this term refers to the mixing and distribution of fuel and oxidant during heating mode, and not to any particular function during pyrolysis mode even though a mixing/distribution apparatus may be present in zone 5 during pyrolysis mode. Downstream of the pyrolysis zone, the pyrolysis products (e.g., unreacted and reacted hydrocarbons) typically flow through a quenching zone, which reduces the temperature of the pyrolysis products to prevent over-cracking, which might otherwise lead to the production of less desired products such as coke. For example, pyrolysis products can flow through the same passages in the RFR's thermal mass as are used for conveying fuel and oxidant in the reverse-flow direction during heating mode. Referring again to FIG. 1B, the channels of first thermal mass 4 typically function as a quench zone during pyrolysis mode. The average temperature within the quenching zone is less than the peak pyrolysis temperature range of the reaction zone, such as being at least 50° C., at least 100° C., or at least 200° C. less than the peak pyrolysis temperature in the pyrolysis zone. Typically the quench temperature is selected to achieve the desired product yield ratios (e.g., olefinic compounds such as ethylene and/or aromatic compounds such as benzene, toluene, xylenes, and naphthalene). The pyrolysis products can be removed from the pyrolysis quenching zone, and further passed out of the RFR for processing in recovery units to process and separate all or select olefinic and/or aromatic compounds.

Pyrolysis mode is typically operated to achieve a desired/peak pyrolysis temperature range in the pyrolysis zone that is effective for producing high quantities of olefins and/or aromatics from hydrocarbon in the pyrolysis feed, such as compared to typical pyrolysis reactions. In some aspects, the pyrolysis reactor can be operated to expose a pyrolysis feedstock to a desired pyrolysis temperature of less than 1200° C. in the pyrolysis zone of the reactor, e.g., from 850° C. to 1200° C., from 850° C. to less than 1200° C., from 900° C. to 1150° C., or from 900° C. to 1100° C.

In some aspects, the pyrolysis reactor can be operated at a pressure range effective for producing high quantities of olefins such as ethylene from hydrocarbon in the feed relative to typical pyrolysis reactions. In such aspects, the pyrolysis reactor is operated to expose a pyrolysis feedstock to an effective olefin-producing (or specifically ethylene-producing) temperature within the pyrolysis zone at a pressure range further effective for producing high quantities of olefins (ethylene). In other aspects, the pyrolysis reactor can be operated at a pressure range effective for producing high quantities of aromatic compounds from hydrocarbon in the feed relative to typical pyrolysis reactions. In such aspects, the pyrolysis reactor is operated to expose a pyrolysis feedstock to an effective aromatics-producing temperature within the pyrolysis zone at a pressure range further effective for producing high quantities of benzene, toluene, xylenes, and naphthalenes. In some aspects, the pyrolysis reaction can be highly effective at a pressure condition in which the hydrocarbon in the pyrolysis zone of the reactor has a partial pressure of $\geq 7$ psia (50 kPaa), $\geq 10$ psia (70 kPaa), $\geq 20$ psia (140 kPaa), or $\geq 30$ psia (210 kPaa).

The pyrolysis reaction can be effectively carried out to produce high quantities of olefins and/or aromatics over a wide range of pressures, including relatively high pressures. For example, the pyrolysis reaction can be highly effective at a pressure condition in which the pyrolysis zone of the reactor is at a total pressure of $\geq 5$ psig (30 kPag), $\geq 15$ psig (100 kPag), $\geq 40$ psig (280 kPag), $\geq 80$ psig (550 kPag), or $\geq 120$ psig (830 kPag). For practical considerations on total pressure, the pyrolysis reaction can be carried out at a pressure condition in which the pyrolysis zone of the reactor is at a total pressure of $\leq 500$ psig (3.4 MPag), $\leq 300$ psig (2.1 MPag), or $\leq 150$ psig (1.0 MPag).

Total gas residence time for the pyrolysis gas stream passing through the reaction zone can be particularly short at higher temperatures in order to produce greater quantities of the desired olefins and/or aromatics. Preferably, the RFR is configured so that pyrolysis feed encounters a temperature greater than 800° C. for a relatively short residence time, particularly relative to residence times typical for making coke. For example, the pyrolysis feed can have a total gas residence time above 800° C. in the RFR of $\leq 5.00$ seconds, such as $\leq 3.00$ seconds, $\leq 1.00$ second, $\leq 0.700$ second, $\leq 0.500$ second, $\leq 0.300$ second, $\leq 0.100$ second, $\leq 0.050$ second, in the range of 0.001 second to 5.00 seconds, in the range of 0.002 second to 1.00 second, or in the range of 0.002 second to 0.300 second. Total gas residence time for the pyrolysis gas stream (i.e., total gas comprising the feed and product components) within the reactor volume (reaction zone volume+first void volume+second void volume) also can be relatively short. For example, pyrolysis feed can be passed through the second thermal mass 6 of the RFR of FIG. 1B at a total gas residence time of $\leq 10$ seconds, $\leq 7.0$ seconds, $\leq 5.0$ seconds, $\leq 3.0$ seconds, $\leq 2.0$ seconds, $\leq 1.0$ second, $\leq 0.8$ second, $\leq 0.75$ second, $\leq 0.6$ second, in the range of 0.001 second to 10 seconds, in the range of 0.01 second to 5.0 seconds, or in the range of 0.01 second to 1.0 second.

Since poppet valves are positioned differently with respect to the inner faces of the reactor's opposed flanges in design A as compared with design B, residence times outside of the reaction zone but within the reactor volume typically are also different. Those skilled in the art will appreciate that residence times within and outside of the reaction zone will depend, e.g., on the extent of the reaction zone within the RFR's internal volume. For example, certain RFR's, have a headspace, and outage, and a reaction zone corresponding to a channeled thermal mass located between the headspace and the outage. For example, when the total gas residence time is in the range of from 350 ms to 450 ms in such an RFR, the ratio $RT_1$ of headspace residence time:reaction zone residence time and (A) the ratio $RT_2$ of outage residence time to reaction zone residence times are typically (B) for design A, $RT_1$ can be in the range of from 0.05 to 0.5 and $RT_2$ in the range of 0.1 to 0.8; and (ii) for design B, $RT_1$ can be in the range of about 0.01 to 0.2, and $RT_2$ is in the range of from 0.05 to 0.4. Alternatively, when the total gas residence time is in the range of from 50 ms to 150 ms, $RT_1$ can be in the range of from 0.4 to 1.6 and $RT_2$ can be in the range of 0.8 to 3.2; and (ii) for design B, $RT_1$ is in the range of about 0.15 to 0.75, and $RT_2$ is in the range of from 0.35 to 1.5.

Pyrolysis mode temperature, pressure, residence time, and $t_P$ can be the same as those disclosed in U.S. Pat. No. 9,499,457 and in P.C.T. Patent Application No. PCT/US2017/046937, particularly when the desired pyrolysis products comprise $C_{4-}$ olefin.

In various aspects, it can be desirable to reduce/minimize pressure drop across the RFR (and in particular across a reaction zone of the RFR) during most reaction steps/modes, but particularly during the pyrolysis mode. Different reaction processes may have different pressure drop sensitivities. For example, in certain aspects, the pressure drop across the reaction zone, whether in each mode or only during the pyrolysis mode, can be 30 psig (210 kPag) or less, e.g., 25 psig (170 kPag) or less, 20 psig (140 kPag) or less, 15 psig (100 kPag) or less, 10 psig (70 kPag) or less, 5 psig (30 kPag) or less, or 2 psig (10 kPag) or less.

In various aspects, in order to achieve relatively stable component flow patterns/distributions (optimally unchanging during any given step/mode), it can be desirable to achieve at least a threshold ratio of a pressure drop across the reaction zone to an axial kinetic energy density at the inlet(s) (e.g., poppet valves) to the RFR body (at the entrance to the first and/or second void spaces) during most reaction steps/modes, but particularly during the pyrolysis mode. As used herein, "axial kinetic energy density" is defined in terms of an axial fluid velocity at the inlet(s) (e.g., poppet valve(s)), Vz,inlet, and a density, ρ; specifically, axial kinetic energy density equals $(\rho*[Vz,inlet]^2/2)$. The threshold ratio of pressure drop across the reaction zone to axial kinetic energy density can be at least 5, e.g., at least 10, at least 15, at least 20, at least 25, at least 30, at least 35, or at least 40. Without being bound by theory, it is believed that, above a certain threshold ratio, component flow patterns can stabilize, such that distribution (perhaps expressed via maldistribution parameter) can be relatively constant or repeatable. As such, there need not be a maximum imposed on threshold ratio of pressure drop across the reaction zone to axial kinetic energy density; nevertheless, optionally the threshold ratio of a pressure drop across the reaction zone to an axial kinetic energy density can additionally be 1000 or less, e.g., 500 or less, 100 or less, 80 or less, 70 or less, 60 or less, 50 or less, 40 or less, 35 or less, or 30 or less. Thus, in various aspects, it can be desirable to achieve a relatively low maldistribution parameter (ratio of pressure drop to axial kinetic energy density) during most reaction steps/modes, but particularly during the pyrolysis mode. A relatively low maldistribution parameter can be 15% or less, e.g., 14% or less, 13% or less, 12% or less, 11% or less, 10% or less, 9% or less, 8% or less, 7% or less, 6% or less, 5% or less, 4% or less, or 3% or less.

A substantial amount of desired products, e.g., olefinic and/or aromatic compounds, can be produced at the appropriate temperature, pressure and contact conditions as noted herein. For example, the pyrolysis feedstock can be exposed at the appropriate temperature, pressure and contact conditions to convert ≥10 wt. %, ≥20 wt. %, ≥30 wt. %, ≥40 wt. %, or ≥50 wt. % of total hydrocarbon in the feedstock to desired products. In some aspects, the olefinic and/or aromatic compounds can have an ethylene:acetylene molar ratio of ≥1:1, ≥5:1, ≥10:1, or ≥15:1.

Pyrolysis Feed

A pyrolysis feed is injected into the RFR for pyrolysis during pyrolysis mode to produce a pyrolysis product comprising hydrocarbon, e.g., olefinic and/or aromatic compounds. The hydrocarbons in the pyrolysis feed can be derived from any hydrocarbon feed capable of being thermally cracked into olefinic and/or aromatic compounds. The hydrocarbons may be optionally treated for use as pyrolysis feed, or a component thereof. Suitable pyrolysis feeds are disclosed, e.g., in U.S. Pat. No. 9,499,457 and in P.C.T. Patent Application No. PCT/US2017/046937.

Pyrolysis Products

The pyrolysis product, also referred to herein as a product mixture, is the effluent mixture from the pyrolysis reaction zone. The pyrolysis product can typically comprise unreacted pyrolysis feed, olefinic and/or aromatic compounds (e.g., ethylene, acetylene, propylene, 1-butene, 2-butene, 1,4-butadiene, benzene, toluene, o-xylene, m-xylene, p-xylene, ethylbenzene, styrene, α-methylstyrene, mesitylene, 1,2,3-trimethylbenzene, 1,2,4-trimethylbenzene, cumene, naphthalene, methylnaphthalene, and mixtures thereof), optionally other saturated hydrocarbons different from the unreacted feed, optional diluent, non-volatiles, etc.

In some aspects, the pyrolysis product can have a relatively high molar ratio of alkene to alkyne (e.g., ethylene to acetylene), such as at a respective molar ratio of ≥2:1, ≥5:1, or ≥10:1. Additionally or alternatively, in some aspects, the pyrolysis product can have a relatively high content of aromatic compounds (e.g., benzene, toluene, o-xylene, m-xylene, p-xylene, ethylbenzene, styrene, α-methylstyrene, mesitylene, 1,2,3-trimethylbenzene, 1,2,4-trimethylbenzene, cumene, naphthalene, methylnaphthalene, and mixtures thereof), such as ≥30 wt. %, ≥35 wt. %, ≥40 wt. %, ≥45 wt. %, ≥50 wt. %, ≥55 wt. %, ≥60 wt. %, ≥65 wt. %, ≥70 wt. %, or ≥75 wt. % aromatic compounds, based on total weight of the pyrolysis product as it emerges from the pyrolysis reactor. Further additionally or alternatively, in some aspects, the pyrolysis product can have a relatively high content of (selectivity for) certain aromatic compounds (e.g., benzene, toluene, o-xylene, p-xylene, naphthalene, and mixtures thereof), such as ≥20 wt. %, ≥25 wt. %, ≥30 wt. %, ≥35 wt. %, ≥40 wt. %, ≥45 wt. %, ≥50 wt. %, ≥55 wt. %, ≥60 wt. %, or ≥65 wt. % of those certain aromatic compounds, based on total weight of the pyrolysis product as it emerges from the pyrolysis reactor.

RFR Purge Mode

Because an oxidant is (cyclically) introduced into the reaction zone during the heating mode, residual oxidant could remain in the reaction zone, which can affect different reactions, depending on the residual oxidant levels and the sensitivity of such reactions to oxidants. Some hydrocarbon conversion processes, such as some pyrolysis processes (e.g., ethane cracking), can be particularly sensitive to, and detrimentally affected by, even relatively low levels of residual oxidant, which is termed "fouling". As a result, a purge mode can be introduced to purge the reaction zone of residual oxidant down to a sufficiently low level, again depending on the sensitivity required for the (cyclic) pyrolysis mode to attain the requisite or desired levels of desirable pyrolysis products. In the purge mode, a fluid (typically a gas and typically relatively inert to the process, such as water/steam, nitrogen, or the like, or a combination thereof) can be introduced into the reaction zone to flush/carry away residual oxidant (oxygen) and/or residual partially/completely oxidized hydrocarbons left from the heating mode.

The sweep efficiency of the purge mode can be evaluated in several ways, such as a volume of purge gas necessary to achieve a target maximum oxidant concentration at an outlet of the RFR body (though the reaction zone boundary is usually the relevant location, measurement is usually much more convenient at the flue gas/purge outlet port(s)/valve (s)). The target maximum oxidant concentration, as mentioned with regard to the heating mode, can depend on the sensitivity of the (cyclic) hydrocarbon conversion (pyrolysis) reaction and/or on the desired product selectivity and/or purity.

In order to best compare purge gas sweep efficiencies between reactors or reaction zones of different size/volume, the purge gas volume can be normalized by the volume of the bed, or the reaction zone, and is typically specified at the particular conditions (e.g., temperature and pressure) of the bed/reaction zone. In various aspects, in the purge mode, residual oxidant can be purged from the reaction zone using less than 7.0 (e.g., less than 6.5, less than 6.0, less than 5.5, less than 5.0, less than 4.5, less than 4.2, less than 4.0, less than 3.8, less than 3.5, less than 3.2, less than 3.0, or less than 2.8) bed volumes of purge gas from at least one of the one or more purge feeds. For reasonable/practical residual oxidant concentrations for hydrocarbon conversion reactions such as pyrolysis, the purge gas volume is typically no lower than 1.0 bed volume; in some aspects, residual oxidant can be purged from the reaction zone using at least 1.2 (e.g., at least 1.5, at least 1.8, at least 2.0, at least 2.2, at least 2.5, at least 2.8, at least 3.0, at least 3.2, at least 3.5, at least 3.8, at least 4.0, at least 4.2, at least 4.5, or at least 5.0) bed volumes of purge gas from the at least one of the one or more purge feeds. Although desired/acceptable residual oxidant concentrations can vary in pyrolysis reactions, some residual oxidant (oxygen) concentrations can be, for example, 20000 ppm (by mole), 10000 ppm, 5000 ppm, 2000 ppm, 1000 ppm, 750 ppm, 500 ppm, 300 ppm, 200 ppm, 100 ppm, 50 ppm, 20 ppm, or 10 ppm.

In various aspects, it can be desirable to reduce/minimize pressure drop across the RFR (an in particular across a reaction zone of the RFR) during most reaction steps/modes, but particularly during heating mode and/or purge mode. Different reaction processes may have different pressure drop sensitivities. For example, in certain aspects, the pressure drop across the reaction zone, whether in every step/mode or only during the heating and/or purge modes, can be 30 psig (270 kPag) or less, e.g., 25 psig (170 kPag) or less, 20 psig (140 kPag) or less, 15 psig (100 kPag) or less, 10 psig (69 kPag) or less, 5 psig (30 kPag) or less, or 2 psig (10 kPag) or less.

In various aspects, it can be desirable to achieve a relatively low maldistribution parameter during most reaction steps/modes, but particularly during heating and/or purge steps/modes. A relatively low maldistribution parameter in purge mode can be 15% or less, e.g., 14% or less, 13% or less, 12% or less, 11% or less, 10% or less, 9% or less, 8% or less, 7% or less, 6% or less, 5% or less, 4% or less, or 3% or less.

In various aspects, in order to achieve relatively stable component flow patterns/distributions (optimally unchanging during any given step/mode), it can be desirable to achieve at least a threshold ratio of a pressure drop across the reaction zone to an axial kinetic energy density at the inlet(s) (e.g., poppet valves) to the RFR body (at the entrance to the first and/or second void spaces) during most reaction steps/modes, such as during the purge mode. The threshold ratio of pressure drop across the reaction zone to axial kinetic energy density can be at least 5, e.g., at least 10, at least 15, at least 20, at least 25, at least 30, at least 35, or at least 40. There need not be a maximum imposed on threshold ratio of pressure drop across the reaction zone to axial kinetic energy density; nevertheless, optionally the threshold ratio of a pressure drop across the reaction zone to an axial kinetic energy density can additionally be 1000 or less, e.g., 500 or less, 100 or less, 80 or less, 70 or less, 60 or less, 50 or less, 40 or less, 35 or less, or 30 or less. Thus, in various aspects, it can be desirable to achieve a relatively low maldistribution parameter (ratio of pressure drop to axial kinetic energy density) during most reaction steps/modes, but particularly during the heating mode. A relatively low maldistribution parameter can be 15% or less, e.g., 14% or less, 13% or less, 12% or less, 11% or less, 10% or less, 9% or less, 8% or less, 7% or less, 6% or less, 5% or less, 4% or less, or 3% or less.

EXAMPLES

All examples herein utilize the RFR of FIGS. 1A and 1B, but with the following changes: (i) the first, second, and third pyrolysis product lines (and associated valves and valve seats) attached to first flange 102 are present but for simplicity are not shown, (ii) first purge line 111 and its associated valve and valve seat) attached to first flange 102 are present but not shown, (iii) one channeled thermal mass replaces first channeled thermal mass 4, second channeled thermal mass 6, and mixing/distribution zone 5, the channeled thermal mass having the form of a circular tube having a central axis (vertical and including at least two other vertical planes of symmetry, as well as a horizontal plane of symmetry perpendicular to the central axis), (iv) a support structure and a flow distributor are added to support the thermal mass, the support structure being located in a second void space between the inner face of second flange 3 and the opposed outer face of the thermal mass, (v) a fuel plenum and a flow distributor are added in a first void space between the inner face of first flange 2 and the opposed face of the thermal mass, and (vi) two additional lines for removing combustion products are connected to second flange 3 (with associated valves and valve seats), these being positioned as shown in FIGS. 3A and 3B. This simplified RFR (analogous to the foregoing alternative RFR) has the form of a circular tube having a central axis (vertical and including at least two other vertical planes of symmetry, as well as a horizontal plane of symmetry perpendicular to the central axis). The channeled thermal mass has the form of a cylinder having a diameter of approximately a 12 foot (approximately 3.7 meter), and contains an array of substantially one-dimensional plug-flow passages. First oxidant line and second oxidant line (and their associated valves and valve seats) are arranged asymmetrically with respect to the central axis. The fuel plenum is a sealed manifold to distribute fuel and which contains pass-through holes to allow pressure equalization and intimate component mixing/distribution). Although these examples are carried out by simulations using the simplified RFR, the results of these simulations are fully applicable to the more generalized RFR of FIGS. 1 A and B.

In the Examples, at least the pyrolysis feed ports, the pyrolysis product ports, the oxidant ports, the flue gas ports, and the purge ports of the RFR have poppet valves that open inward toward the reaction zone (into the first or second void space, or even into the support structure volume, as the case may be). Each such port exhibits a valve head diameter A, a valve rim thickness C, a valve head clearance D, a valve shaft diameter E, a valve inlet/outlet diameter F; and optionally a connection between valve recesses at height G, as illustrated in FIGS. 2A-2B. The first void space has an axial height B1 (not shown), the second void space has an axial height B2 (not shown), and the support structure volume has an axial height BS (not shown).

RFR apparatus designs A and B, as identified in FIGS. 2A and 2B, are compared and contrasted in these Examples, with changing pyrolysis process goals indicating different reactor design choices, or, alternately expressed, with different reactor design choices driving different process/product characteristics. FIGS. 3A-B show additional external perspective views of the RFR designs A and B, respectively.

As flow maldistribution can be a serious consideration during heating mode and pyrolysis mode, it is important to note that the asymmetric nature of the flow/piping in both designs would be thought to significantly complicate that goal, as would a decrease in void space volume available for normalizing flow distributions. It should be noted that even relatively compact void space volumes, unexpectedly, still can result in relatively uniform (low maldistribution) flow patterns.

Example 1—Design A Vs. Design B: Reducing Maldistribution During Heating Mode

In Example 1, the primary goal is to reduce or minimize maldistribution of flow paths regarding the combustion reaction, thus during heating mode. The differences between designs A and B are largely within the headspace (first void volume) and the outage (second void volume). Table 1 below shows the characteristic measurements relating to the valving of the ports in each design, to highlight the difference between designs A and B.

TABLE 1

| Parameter | Letter (from FIGS. 2A-2B or specification) | Units | Design A | Design B |
|---|---|---|---|---|
| Valve Diameter | A | cm | 49.5 | 49.5 |
| Headspace Height | B1 | cm | 20.7 | 20.7 |
| Valve Rim Thickness | C | cm | 3.26 | 3.26 |
| Valve Clearance | D | cm | 5.08 | 5.08 |
| Shaft Diameter | E | cm | 9.90 | 9.90 |
| Inlet Diameter | F | cm | 41.7 | 41.7 |
| Height of Passages between Valve Recesses* | G | cm | N/A | 6.92 |
| Reactor Effective Diameter | Z | cm | 366 | 366 |
| Reactor Volume | | $m^3$ | 38.4 | 38.4 |
| Steam Purge Valve Diameter | | cm | 27.5 | 27.5 |
| Headspace Volume | | $m^3$ | 2.2 | 1.0 |
| Support Structure Beam Height | BS | cm | 20.3 | 20.3 |
| Outage Height (below beams) | B2 | cm | 15.2 | 0** |
| Lower Void Volume (Outage + Beams) | | $m^3$ | 4.3 | 2.1 |

*semi-circular pipes connecting valve recesses (see FIG. 2B);
**in design B, there is no outage, and open valves extend in between beams in the support structure volume to minimize void space.

FIGS. 4A-4D show maldistribution parameters from ethane pyrolysis in the RFRs of designs A and B, as accomplished during computational fluid dynamics (CFD) simulations. Table 2 below shows the CFD conditions in the headspace/outage used to simulate each step/mode of the ethane pyrolysis reaction.

TABLE 2

| Parameter | Units | Pyrolysis Mode | Heating Mode | Purge Mode |
|---|---|---|---|---|
| Flow rate | Mg/hr | 212 | 216 | 27.9 |
| Temperature | degrees C. | 200 | 200 | 200 |
| Pressure | psig [kPag] | 27 [190] | 18 [120] | 22 [150] |
| Density | $kg/m^3$ | 2.20 | 1.62 | 2.10 |
| Viscosity | Pa·s | 1.73E−05 | 2.76E−05 | 1.63E−05 |
| Bed ΔP | psi [kPa] | 5.0 [35] | 7.5 [52] | 0.47 [3.2] |

Figure 4A:
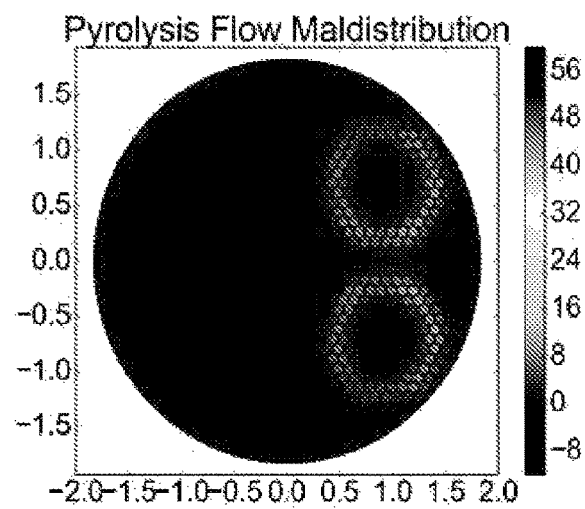
FIGS. 4A-4D each show normalized velocity fields, relative to an average flow velocity, within a cross-section of a monolithic channeled thermal mass located in a RFR reaction zone. The velocity fields represent differences between local axial velocity over each 4-inch (10-cm) simulated stack and the axial mean reactor velocity.
Figure 4B:
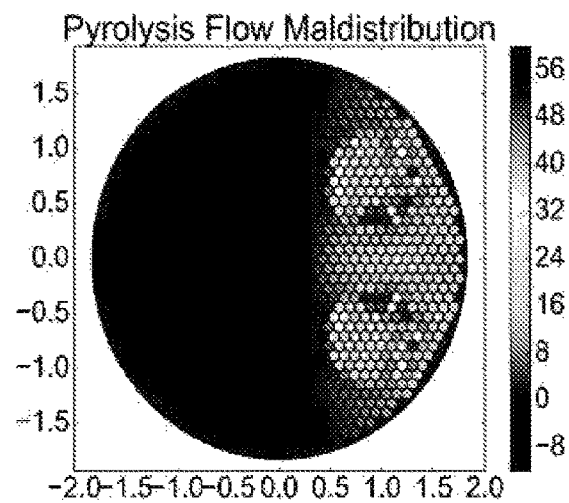
Figure 4C:
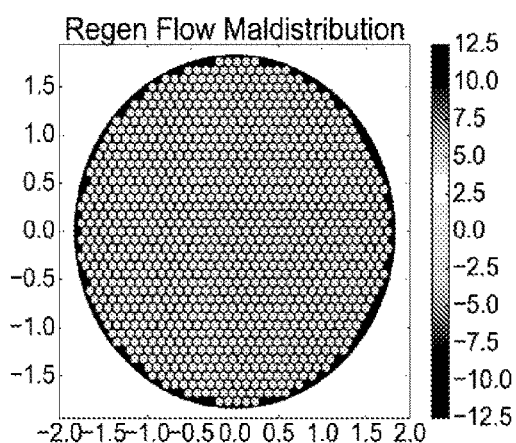
Figure 4D:
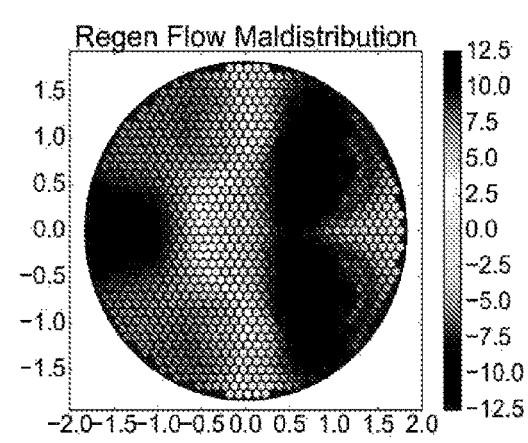
Figure 5A:
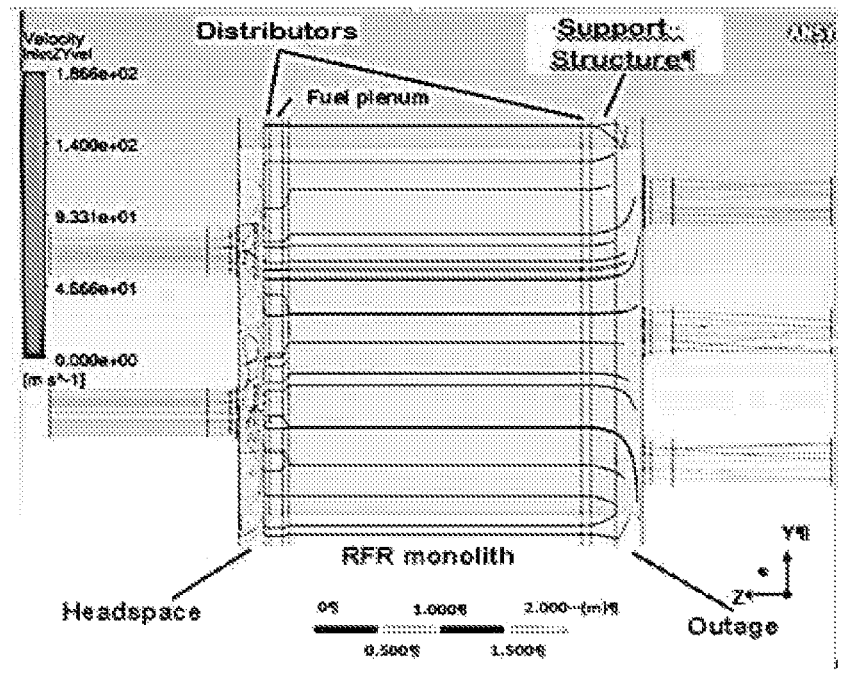
FIGS. 5A-5B graphically show simulated flow patterns within an RFR apparatus during the heating mode for RFR design A (from FIGS. 2A and 3A) in side view and perspective view, respectively, with streamlines showing stream flow entering on the left side.
Figure 5B:
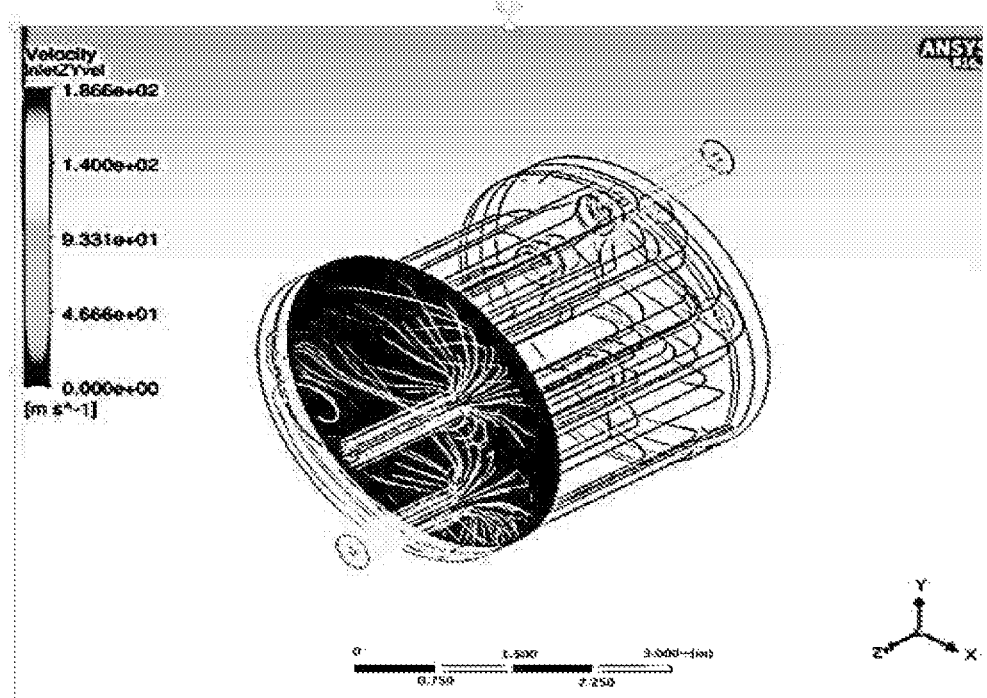

The plots in FIGS. 4A-4D each show normalized velocity fields, relative to an average flow velocity, within a cross-section of the monolithic reaction zone representing the differences between local axial velocity over each 4-inch (10-cm) simulated stack and the axial mean reactor velocity (defined as $\{[Vz(x,y)-<Vz>]/<Vz>*100\%\}$). FIGS. 4A-4B show maldistribution parameters during the pyrolysis mode in designs A and B, respectively, while FIGS. 4C-4D show maldistribution parameters during the heating mode in designs A and B respectively. As can be seen, FIG. 4C shows a relatively uniform flow distribution in design A during the heating mode, with relatively little maldistribution. Though FIG. 4D does show some moderate maldistribution due to the flow asymmetry, it is believed to be quite surprising that the maldistribution is not more severe, due to the miniscule (essentially zero) outage in design B. Indeed, simulated flow patterns within the RFR apparatus during the heating mode for design A are shown graphically in side view and perspective view in FIGS. 5A and 5B, respectively, with streamlines showing oxygen-containing stream flow entering on the left side in each Figure.

Although a relatively important parameter in many reactions, it was surprising that pressure drop across the reaction zone was observed to be such a sensitive parameter in the assessment of maldistribution in the reactor designs. This result can be seen particularly well in FIG. 6, though aspects of it may be apparent from FIGS. 4A-4D and 5A-5B. FIG. 6 shows a plot of overall maldistribution (in axial fluid velocity) against a ratio of total pressure drop across the RFR body/reaction zone (represented by ΔPtot; the support structure and the fuel plenum in both designs are believed to have negligible contribution to pressure drop due to their high voidage, >20%, and low thickness, <21 cm) to axial kinetic energy density (represented by $\{\rho*[Vz,inlet]^2/2\}$. The Figure shows numerical values of maldistribution parameters for simulated pyrolysis mode (solid squares) for designs A and B, as well as for heating mode (solid triangles) for designs A and B; in addition, the Figure shows how the maldistribution parameters change for lower pressure drop scenarios in design A (dotted line progression).

It can be seen that design A seems to provide relatively uniform (low) maldistribution parameters for both pyrolysis and heating steps/modes, which both appeared significantly lower than for design B. It can be said that design B can sacrifice some flow distribution in order to significantly reduce the reactor void volume (see Table 1). It should be noted that particularly design A achieves a relatively uniform flow even in the simplified reactor configuration (e.g., the reactor of FIGS. 3 A and B) without the need for a second channeled thermal mass or a mixer-distributor located between thermal masses as may be needed in the RFRs of FIGS. 1 A and B. Advantageously, both designs A and B appear to enable an ethane pyrolysis RFK apparatus to use very few valves, even asymmetrically placed, thereby substantially reducing valving and piping layout costs, as compared to more symmetric and/or more prolific ported reactor designs. Table 3 below enumerates the various pressure drops and axial kinetic energy densities for the various steps/modes in ethane pyrolysis reactions using reactor designs A and B (all in psi units, with kPa units in brackets).

TABLE 3

| Step/Mode | void volume | Design A moderate | Design B low |
|---|---|---|---|
| Pyrolysis | ΔP, bed | 5.0 [35] | 5.0 [35] |
| | ρ [Vz, valve]$^2$/2 | 0.19 [1.3] | 0.19 [1.3] |
| | ΔP, distributors | 0.19 [1.3] | 0.19 [1.3] |
| Heating | ΔP, bed | 7.5 [52] | 7.5 [52] |
| | ρ [Vz, valve]$^2$/2 | 0.27 [1.9] | 0.27 [1.9] |
| | ΔP, distributors | 0.45 [3.1] | 0.45 [3.1] |
| Purge (Steam Sweep) | ΔP, bed | 0.47 [3.2] | 0.47 [3.2] |
| | ρ [Vz, valve]$^2$/2 | 0.15 [1.0] | 0.15 [1.0] |
| | ΔP, distributors | 0.037 [0.26] | 0.037 [0.26] |

Additionally, without being bound by theory, FIG. 6 shows a rather unexpected interrelationship between flow maldistribution and pressure drop. As shown by FIG. 6, increasing the ratio between pressure drop and flow kinetic energy density can include a cost, namely higher pressure drop may be needed to maintain a similar maldistribution or larger voidage may be necessary, if pressure drop is not easily manipulable (e.g., by changing reactor internals during operation). Indeed, FIG. 6 shows that there is an approximate point of diminishing returns beyond which decreasing kinetic energy density or increasing bed pressure drop seems to result in minimal or no substantial gain in maldistribution parameter. It should also be noted from the low pressure drop series of simulations in FIG. 6 that increasing kinetic energy density (denominator) or reducing pressure drop (numerator) excessively can lead to a significant increase in maldistribution parameter, which link between pressure drop reduction and maldistribution parameter was not believed to be previously known or well-understood.

Example 2—Design A vs. Design B: Increasing Steam Sweep Efficiency During Purge Mode In Example 2, the primary goal is to reduce or minimize maldistribution of flow paths regarding the steam sweep portion of the purge mode, which effectively includes reducing or minimizing the total volume between the ports/valves and the monolithic reaction zone. Enabling relatively short purge times (or, at a given purge rate, relatively short purge volumes) and relatively rapid switching between steps/modes (before/after purge mode). As a reminder, the characteristic measurements relating to the valving of the ports in each of designs A and B are shown in Table 1; the CFD conditions used to simulate each step/mode of the ethane pyrolysis reaction are shown in Table 2; and the various pressure drops and axial kinetic energy densities for the various steps/modes are shown in Table 3.

Simulated flow patterns within the RFR during the purge (steam sweep) mode of ethane pyrolysis for design A are shown graphically in perspective view and end view in FIGS. 7A and 7B, respectively, with streamlines showing purge gas (steam) entering on the left side in FIG. 7A and exiting through three flue gas ports (see FIGS. 1A-1B and 2A-2B).

Figure 8:
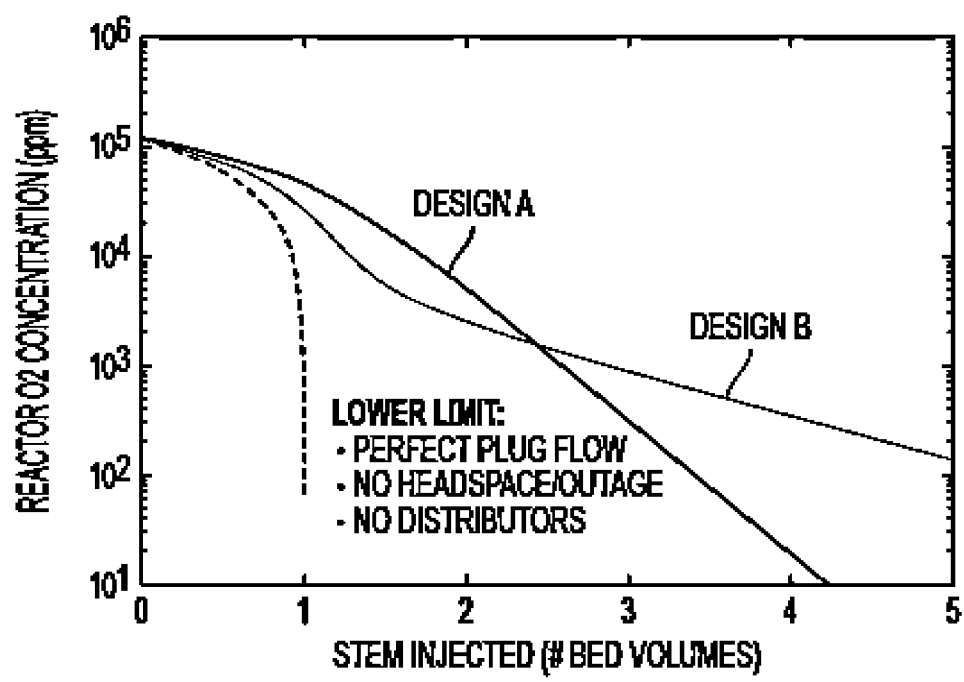
FIG. 8 shows a plot of computational fluid dynamics (CFD) simulated reaction zone oxygen concentration versus a volume of purge gas injected into an RFR for various RFR designs.

Although a relatively important parameter in many reactions, it was surprising that pressure drop across the RFR body/reaction zone was observed to be such a sensitive parameter in the assessment of purge (steam sweep) efficiency in the reactor designs. This result can be seen particularly well in FIG. 8, though aspects of it may be apparent from FIGS. 7A-7B. FIG. 8 shows a plot of CFD-simulated reaction zone oxygen concentration (ppm) against a volume of steam (purge gas) injected into the RFR body/reaction zone (represented as normalized by the bed volume, or the fluid-containing volume of the RFR body/reaction zone at reaction temperatures and pressures), based on an imputed ~400-millisecond pyrolysis residence time. As before, the support structure and the fuel plenum in both designs are believed to have negligible contribution to pressure drop due to their high voidage, >20%, and low thickness, <21 cm. The Figure shows simulated trend lines for decreasing reactor oxygen concentration with increasing purge gas (steam) volume in the purge mode for designs A and B, as well as a theoretical lower limit of purge gas volume required in a theoretical design having no headspace, no outage, and no mixers/flow distributors, as well as perfect plug flow conditions (dotted line). Although the x-axis of FIG. 8 is expressed in units of bed volume, it may alternatively be expressed in units of bed residence time, e.g., by purging for a time that is a pre-determined multiple of the total bed residence time.

It can be seen that design A seems to be better able than design B to achieve lower reactor oxygen concentrations with similar gas bed volumes in the purge mode, at or below about 2000 ppm. Said another way, it appears that design A provides increased sweep efficiency at or below about 2000 ppm reactor oxygen concentration (lower number of bed volumes of gas needed to attain reactor oxygen concentrations at or below 2000 ppm). On the other hand, the result seems to be reversed (design B being better than design A) with respect to increased sweep efficiencies at target reactor oxygen concentrations above about 2000 ppm (in FIG. 8, up to about 100000 ppm). These results are counterintuitive, particularly with respect to the seemingly arbitrary oxygen concentration where design considerations seem to shift. Without being bound by theory, the seemingly arbitrary "critical" reactor oxygen concentration may be related to the number and/or extent of fluid recirculation volumes within the reaction zone. One counterintuitive aspect of these results includes the suggestion that backmixing or dead zones may become increasingly important to account for as more oxygen is removed from the RFR body/reaction zone. These findings further allow a skilled artisan to better select RFK design criteria to match the needs of a particular pyrolysis reaction.

Also without being bound by theory, the relatively confined geometry of design B (reduced void space) may result in the purge gas (steam) having difficulty reaching tight and/or remote spaces far from the purge gas inlet valve. Nevertheless, it can be said that design A can sacrifice some purge sweep efficiency in order to significantly reduce the reactor maldistribution. Both designs A and B appear to enable an ethane pyrolysis RFK apparatus to use very few valves, even asymmetrically placed, thereby substantially reducing valving and piping layout costs, as compared to more symmetric and/or more prolific ported reactor designs.

For ethane pyrolysis/cracking reactions, the pyrolysis product slate is particularly highly sensitive to even rather low reactor oxygen concentrations (presumably because of the desirability of olefins as products and/or as intermediates to aromatic products). Thus, rather deep purges and low residual reactor oxygen concentrations (e.g., about 10 ppm oxygen at the reaction zone/reactor exit/flue gas valve(s), which, averaged over the cycle, reduces to about 1 ppm oxygen) may be required for practical commercial considerations in such ethane pyrolysis/cracking reactions. Such situations implicate design A for reasonable purge times/gas volumes. For other reaction chemistries (e.g., steam reforming of methane to syngas), however, the sensitivity to residual oxygen concentration can be greatly reduced, meaning that design B may be feasible in such cases, and may be particularly advantageous in aspects where it is desired to rapidly switch from one mode to another, e.g., from pyrolysis mode to heating mode, and/or when total residence time is ≤300 ms, such as ≤100 ms.

All documents described herein are incorporated by reference herein for purposes of all jurisdictions where such practice is allowed, including any priority documents, related applications, and/or testing procedures to the extent they are not inconsistent with this text, provided however that any priority document not named in the initially filed application or filing documents is not incorporated by reference herein. Although forms of the invention have been illustrated and described, various modifications can be made without departing from the spirit and scope of the invention. Individual elements or features of a particular aspect are generally not limited to that particular aspect, but, where applicable, are interchangeable and can be used in a selected aspect, even if not specifically shown or described. Variations are not to be regarded as a departure from the disclosure, and all such modifications are intended to be included within the scope of the disclosure. Accordingly, it is not intended that the invention be limited thereby. Also, whenever a composition, an element, or a group of elements is preceded with the transitional phrase "comprising," it should be understood that the same composition or group of elements is contemplated with transitional phrases "consisting essentially of," "consisting of," "selected from the group of consisting of," or "is" preceding the recitation of the composition, element, or elements, and vice versa. All numerical values within the detailed description and the claims herein are modified by "about" or "approximately" the indicated value, and take into account experimental error and variations that would be expected by a person having ordinary skill in the art.

What is claimed is:

1. A method of transforming a hydrocarbon feed into a pyrolysed product in a reverse flow reactor (RFR) apparatus exhibiting an asymmetric heating feed profile and a low maldistribution parameter, the method comprising:
   providing an RFR apparatus comprising an RFR body, a reaction zone located within the RFR body, at least two oxygen-containing feeds, a combustion fuel feed, a purge feed, and a pyrolysis feed which comprises hydrocarbon, at least 60 mol % of which comprise $C_{2+}$ hydrocarbon compounds, wherein (i) the reaction zone has a central vertical axis and is flanked by first and second void spaces and (ii) the reaction zone includes at least one bed having the form of a monolith having a plurality of discrete passages extending axially therethrough;
   operating the RFR apparatus to cycle between an exothermic heating mode, a purge mode, and an endothermic pyrolysis mode so as to attain substantially hydrocarbon pyrolysis products;
   in the heating mode, heating the reaction zone to a temperature of at least 700° C. by reacting the combustion fuel feed with the oxygen-containing feeds while maintaining a pressure drop across the reaction zone of about 15 psig or less;
   in the purge mode, purging oxygen from the reaction zone using less than 6 bed volumes of the purge feed and under conditions sufficient to maintain a pressure drop across the reaction zone of about 5 psig or less; and
   in the pyrolysis mode, exposing the hydrocarbons in the pyrolysis feed to a temperature and flow conditions and for a time sufficient to pyrolyse the hydrocarbons to form the pyrolysis products, while maintaining a pressure drop across the reaction zone of 10 psig or less,
   wherein the heating mode is operated under conditions such that the maldistribution parameter is at 5% or less, and such that a ratio of the pressure drop across the reaction zone to an average axial kinetic energy density of the feeds within the first and second void spaces is at least 10.

2. The method of claim 1, wherein the RFR apparatus further contains a catalyst to facilitate conversion of the hydrocarbons in the pyrolysis feed to form the pyrolysis products.

3. The method of claim 1, further comprising purifying the pyrolysis products to reduce a concentration of one or more first pyrolysis products and/or to enhance a concentration of one or more second pyrolysis products, thereby forming a pyrolysis product.

4. The method of claim 1, wherein the pyrolysis mode is operated under conditions such that the maldistribution parameter is at 10% or less, and such that a ratio of the pressure drop across the reaction zone to an average axial kinetic energy density of the feeds within the first and second void spaces is at least 10.

5. The method of claim 1, wherein less than 15 mol % of the hydrocarbons in the pyrolysis feed comprise $C_1$ hydrocarbons, and at least 50 mol % of the hydrocarbons in the pyrolysis feed comprise $C_2$ hydrocarbons.

6. The method of claim 1, wherein the heating mode is operated so as to maintain the pressure drop across the reaction zone at 10 psig or less, the maldistribution parameter at 2% or less, and the ratio of the pressure drop across the reaction zone to the average axial kinetic energy density of the feeds within the first and second void spaces between 20 and 40.

7. The method of claim 1, wherein the heating mode is operated under conditions such that a catalyst located within the reaction zone is at least partially regenerated, thereby reducing a content of coke on the catalyst to less than 5 wt. %.

8. The method of claim 1, wherein the purging is conducted so as to maintain the pressure drop across the reaction zone at 2 psig or less and to achieve an oxygen level at an outlet of the RFR body of at most 20 ppm in the purge mode, while using 4.5 bed volumes or less of the purge feed.

9. The method of claim 1, wherein the pyrolysis mode is operated so as to maintain the maldistribution parameter at 5% or less, and the ratio of the pressure drop across the reaction zone to the average axial kinetic energy density of the feeds within the first and second void spaces between 20 and 40.

10. The method of claim 1, wherein at least two purge feeds and at least two pyrolysis feeds are present, wherein at least one of the purge feeds comprises steam provided in a flow path countercurrent to the pyrolysis feeds through the reaction zone, and wherein the method thus comprises steam cracking of the hydrocarbons in the pyrolysis feed.

11. The method of claim 3, wherein the one or more second pyrolysis products comprise one or more of ethylene, acetylene, propylene, 1,4-butadiene, benzene, toluene, o-xylene, p-xylene, and naphthalene.

12. The method of claim 3, wherein the one or more first pyrolysis products comprise methane, ethane, propane, butane, and hydrogen.

13. The method of claim 1, wherein the RFR body comprises:
   a first distributor between the first void space and the reaction zone;
   a second distributor between the second void space and the reaction zone; and
   a support structure configured to mechanically support the reaction zone and the first and second distributors and disposed adjacent to the second distributor, such that the support structure is between the reaction zone and the second void space.

14. The method of claim 1, wherein the RFR apparatus comprises:
   two or more oxygen-containing feed ports configured to axially feed the at least two oxygen-containing feeds into the first void space of the RFR body and arranged asymmetrically with respect to the central axis;
   a pyrolysis feed port configured to axially feed the pyrolysis feed containing the hydrocarbons into the second void space of the RFR body;
   a pyrolysis products port configured to axially receive the pyrolysis products from the first void space of the RFR body;
   a flue gas port configured to axially receive by-product fluids from the second void space of the RFR body;
   two or more purge feed ports, at least one configured to axially feed a first portion of the purge feed into the first void space and at least one configured to axially feed a second portion of the purge feed into the second void space; and
   one or more combustion fuel feed ports configured to feed the combustion fuel feed into the reaction zone.

15. The method of claim 14, wherein the RFR apparatus further comprises:
   at least two pyrolysis feed ports arranged asymmetrically with respect to the central axis;
   at least two pyrolysis products ports arranged asymmetrically with respect to the central axis; and
   at least two flue gas ports arranged asymmetrically with respect to the central axis.

16. The method of claim 13, wherein a ratio of a volume of the first void space to a volume of the reaction zone is 0.070 or less, and a ratio of a sum of a volume of the second void space plus the support structure volume to the volume of the reaction zone is 0.16 or less.

* * * * *